US005580761A

United States Patent [19]
Greatbatch et al.

[11] Patent Number: 5,580,761
[45] Date of Patent: *Dec. 3, 1996

[54] METHOD OF CONFERRING RESISTANCE TO IMMUNODEFICIENCY VIRAL INFECTION

[75] Inventors: Wilson Greatbatch, Akron; John C. Sanford, Geneva, both of N.Y.

[73] Assignee: Greatbatch Gen-Aid Ltd., Clarence, N.Y.

[ * ] Notice: The term of this patent shall not extend beyond the expiration date of Pat. No. 5,324,643.

[21] Appl. No.: 217,210

[22] Filed: Mar. 23, 1994

Related U.S. Application Data

[63] Continuation-in-part of Ser. No. 739,718, Jul. 29, 1991, Pat. No. 5,324,643, and Ser. No. 156,188, Feb. 16, 1988, abandoned.

[51] Int. Cl.[6] .......................... C12N 15/11; C12N 5/10; C07H 21/02; C07H 21/04
[52] U.S. Cl. .................. 435/91.32; 435/91.1; 435/91.3; 435/172.3; 435/240.1; 435/240.2; 435/320.1; 536/23.1
[58] Field of Search .............................. 435/172.3, 240.1, 435/240.2, 91.32, 320.1, 91.1, 91.3; 514/23.1

[56] References Cited

U.S. PATENT DOCUMENTS 4,806,463   2/1989   Goodchild et al. .................... 435/5

FOREIGN PATENT DOCUMENTS

WO87/03451   6/1987   WIPO .

OTHER PUBLICATIONS

E. C. M. Mariman (1985) Nature 318:414.
R. Tellier et al. (1985) Nature 318:414.
H. Mitsuya et al. (1987) Nature 325:773–778.
L.-J. Chang et al. (1987) Journal of Virology 61(3):921–924.
M. I. Johnston et al. (1993) Science 260:1286–1293.
S. M. Sullivan et al. (1992) Antisense Research and Development 2:187–197.

*Primary Examiner*—Mindy Fleisher
*Assistant Examiner*—Johnny F. Railey, II
*Attorney, Agent, or Firm*—Hodgson, Russ, Andrews, Woods & Goodyear

[57] ABSTRACT

In accordance with the present invention, disclosed is a method of conferring, upon a host cell, resistance to retroviral infection by interfering with one or more of the infection processes including retroviral replication and assembly into infective viral particles. The method involves introducing a vector into a host cell, wherein the vector comprises a polynucleotide which directs transcription, within the host cell, of RNA which is a) complementary or corresponding, depending on the target region, to a nucleic acid sequence within one or more regions of the genome of the retrovirus; and b) is effective in inhibiting one or more steps in the retroviral infection process by interfering with retroviral replication, reverse transcription, translation, or assembly into viral particles when the host cell is infected. Also disclosed is a method of treatment using the nucleic acid constructs, or cells upon which resistance to infection has been conferred.

40 Claims, 7 Drawing Sheets

FeLV LTR Genome     FIG. 2

```
MLV   CCCTGTGCCTT        ATTTCAACTAACCAATC    A  G  T  TCGCTTCTCGCTTCT
FeLV  AATTCAACCTTCCGTCTCATTTAAACTAACCAATCCCCACGCGTCTCGCTTCT

GTTCGCGCGCTTCCGTCCCCGAGCTCAATAAAA    GAGCCCACAACCCCTCACTCGGCG
                                                         -5
      GTACGCGCGCTT    TCT    GCT  ATAAAAAACGAGCCATCAGCCCC CACA GGCG

CGCCAGTCCTCCGATTGACTGAGTCCCCCGCGTACCCGTGTATCCAATAAACCCTCTTGC
                                                   50
      CGCAAGTCTTTGTTGAGACTTCACCCCCCGCGTACCCGTGTA CGAATAAAGCCTCTTGC

AGTT GCATCCGACTTGTGGTCTCGGTGTTCCTTGGG A   GGGTCTCCTCT  GAGTGA
                                                100
      TGTTTGCATCTGACTCGTGGTCTCGGTGCTCCGTGGGCACGGGGTCTCATCGCGGAG GA

TTGAC TACCCGTCAGCGGGGGTCTTTCATTTGGGGGCTCGTCCGGGATCGGGAGACCCC
                                    150
      A GACCTAC   TC  CGGGGGTCTTTCATTTGGGGGCTCGTCCGGGAT A GAGACCCC

TG   CCCAGGGACCACCGACCCACCACCGGGAGGTAAGCTGGCCAGCAAC TTATCTGTG
                                 200
      CAACCCCAGGGACCACCGACCCACCATCAGGAGGTAAGCTGGCCGGCGACCATATCTGT

TCTGTCCGATTGTCT AGTGTCTATG   ACT      GATTTTATGCGCCTGCGTCGGTA
                                250
        TGTCC  TTGTGTAAGTGTCTCTGTCAACTGATCTGATTTT

LeuThrSerSerValSerGlyGly ProValValGluLeuThrSerSerGlu
      CTAGTTAGCTAACTAGCTCTGTATCTGGCGGA CCCGTGGTGGAACTGACGAGTTCGGAA

GGCGGTGGAACCGAAGGAGCTGACGAGCTCGTAC

HisProAlaAlaThrLeuGlyAspValPro Gly    Thr     SerGlyAlaValPhe
      CACCCGGCCGCAACCCTGGGAGACGTCCCA GGG    ACT     TCGGGGCCGTTTTT

TCCGCCCCCGCAACCCTGGAAGACGTTCCACGGGTGTCTGATGTCTGGAGCC TCT A
                                                       MetSerGlyAla Ser

ValAlaArgProGluSerLysAsnProAspArgPheGlyLeuPheG..
      GTGGCCCGACCTGAGTCCAAAAATCCCGATCGTTTTGGACTCTTTG..

AGTGGG  ACA   G CC ATT GGG GCTCAT    CTGTTTG..
      SerGly  Thr   Ala Ile Gly AlaHis     LeuPheG..
```

METHOD OF CONFERRING RESISTANCE TO IMMUNODEFICIENCY VIRAL INFECTION

CROSS-REFERENCE TO RELATED APPLICATIONS

This application is a continuation-in-part application of our earlier applications U.S. Ser. No. 739,718 filed Jul. 29, 1991, now U.S. Pat. No. 5,324,643; and U.S. Ser. No. 156,188, filed Feb. 16, 1988, now abandoned, which are incorporated herein by reference.

FIELD OF THE INVENTION

The present invention relates generally to the inhibition of retroviral replication and other essential retroviral functions by hybridization interference in a host cell system. More particularly, the invention provides compositions and methods for producing RNA complementary to essential hybridization sites within immunodeficiency viral genomes.

BACKGROUND OF THE INVENTION

Retroviruses are the causative agents for an increasing number of diseases of higher organisms including: AIDS, immunodeficiency syndromes of other mammals, various leukemias, feline leukemia, murine leukemia, several avian leukemias, various sarcomas of mice, rats, monkeys, birds, and cats, and other lymphotrophic diseases of man, including Adult T-Cell leukemia. Acquired Immune Deficiency Syndrome (AIDS), the recently most noteworthy of these diseases, is believed to be caused by a retrovirus which has been called HTLV-III, LAV, RAV or most recently HIV. Coffin et al., Science, 232:697 (1986). HIV is one of a group of retroviral diseases which attacks the T4 lymphocytes thereby destroying the body's immune system. Anderson, Science, 226:401–409 (1984); Weiss, In RNA Tumor Viruses-II, vol. 2, Cold Spring Harbor Laboratory, pp. 405–485 (1985). The disease is uniformly fatal and no cure has been developed which either kills the virus in situ or replaces the lost elements of the body's immune system. Some experimental drugs such as HPA-23, azidothymidine and suramin show limited effects in stopping the virus, and immunomodulators such as thymostimulin and isoprinosine hopefully will bolster the patient's malfunctioning immune system, but to date there is no proven therapy or cure for the AIDS patient. It is also unlikely that a traditional vaccine for the virus will be developed for quite some time due to the wide variation in antigenicity of various strains of the virus.

Retroviral diseases differ from any other viral diseases in that the infective agent, a retrovirus, eventually becomes integrated in the host cell's genome. The retrovirus inserts its genome into a host chromosome, such that its genetic material becomes part of the genetic makeup of the infected cell, and is then replicated with the cell as the cell divides and multiplies. It is this characteristic which makes retroviruses especially persistent and immune to traditional antiviral treatment. There is as yet no way to kill the retrovirus without killing the host cell. Thus, there is no proven cure, nor is there any proven effective vaccine or pharmacological agent against any retroviral disease.

Details of the life cycle and replication of retroviruses are discussed at length in Weiss et al., RNA Tumor Viruses, vols. 1 and 2 (Cold Springs Harbor Laboratory 1984), which is incorporated herein by reference in its entirety. FIG. 1(B) summarizes a model of a retrovirus life cycle. The life cycle of retroviruses is unique among viruses. The cycle begins when an infectious particle enters a host cell and releases two identical RNA molecules. These molecules are "reverse transcribed" by special viral enzymes to produce double-stranded DNA which circularizes and inserts into the host chromosome. FIG. 1(A) summarizes a model of the synthesis of double-strand DNA from viral RNA. The inserted DNA virus or "pro-virus" is structurally very similar to a normal host gene. It is transcribed to produce RNA, like any host gene. This RNA can then be processed in three ways: a) it can be directly translated into certain viral proteins, b) it can be processed and spliced and then translated to produce other viral proteins, or c) it can be packaged, along with various viral proteins to make a newly infectious particle. In the case of HIV, the infectious particles continuously "bud off" the infected cells and bind to uninfected cells, beginning the cycle over again.

The retroviral particle which is the infectious agent contains in its interior two single-stranded positive-sense viral RNA molecules each between 7,000 to 11,000 nucleotide bases in length. These viral RNA's combine with certain viral proteins to form a viral core; the core being surrounded by a membrane. Imbedded in the membrane are viral glycoproteins which can specifically bind the viral particles to the appropriate host cell system. The viral core is assembled within the host cell and exits from the host cell, taking some of the host's membrane with it. Hence the membrane of the viral particle is derived directly from the host cell. The particle travels to an uninfected host cell, and due to the glycoprotein on its exterior binds to the new host cell and the life cycle repeats. Once the virus enters the cell, it is disassembled, releasing the two identical viral RNA molecules. These molecules are each composed of a sequence having specific functional regions making up the viruses "genomic structure".

The genome of any retrovirus is divided into three regions: the 5' terminus, the 3' terminus and a central region containing genes coding for proteins. The 5' terminus is further divided into four functional regions: the terminal redundancy (R), a unique sequence (U5), the primer binding site (PBS) and an untranslated sequence (L). The L region may contain a splice donor site for subgenomic mRNA. The 3' terminus is further divided into three functional regions: the primer-binding site for positive strand DNA synthesis (PB+ or PBS), a unique sequence (U3) and another copy of the terminal redundancy (R). The U5, U3 and R regions are sometimes collectively referred to as the Long Terminal Repeat (LTR) region. Components of the LTR region are involved in integration of the retroviral genome into the genome of its host. All retroviruses contain these highly conserved regions. These regions are further described by Weiss et al. (supra, pp. 262–296).

The production of DNA from the infectious RNA occurs by a complex process called reverse transcription. The viral reverse transcriptase enzyme first complexes with a specific tRNA molecule supplied by the host cello For example, in the case of the AIDS-related virus, it is lysine tRNA which complexes with the reverse transcriptase. The 3' end of the tRNA molecule remains free to hybridize with the primer binding site (PBS) of the retroviral genome. This is a sequence within the virus, which is complementary to the 5' end of the tRNA. Once the virus/enzyme/tRNA complex has been formed, the enzyme can make a new DNA molecule, using the RNA virus as a template, and using the tRNA as a "primer". As the process proceeds, the RNA of the resulting RNA/DNA complex is degraded, leaving single-stranded DNA. This process begins internally at the PBS site and proceeds to the 5' end of the RNA virus, where the process is stalled and regresses slightly, leaving a single-strand DNA "sticky end". At this point the enzyme/DNA complex has to "jump" to a new template at the 3' end of the virus. This jump, termed the first jump, is possible because the newly synthesized DNA is complementary to the other R region at the 3' end of the virus. After this jump, reverse transcription continues around to the point of the primer binding site.

After the "first jump" and while reverse transcription continues, second-strand DNA synthesis begins from the poly-purine site upstream of the U3 region. This DNA second-strand synthesis continues in the opposite direction from the first-strand DNA synthesis and proceeds through the primer binding site. The RNA primer molecule is consequently degraded, leaving a short residual region of second-strand DNA extending from the region of double-strand DNA. At this point the enzyme/DNA complex needs to make a "second jump" to a new template, this time jumping to the "sticky end" of the second strand DNA. This is possible because of complementation between the first and second strand DNA molecules in the region of the primer binding site. After hybridization of the complementary ends, reverse transcription can continue using the second-strand DNA as a template. This subsequently results in displacement of the first strand DNA, past the site of the first jump, up to the point where the second strand synthesis begins. Second-strand synthesis which was stalled at the PBS site prior to the second jump, can also continue after this jump, and proceeds to the 5' end of the first-strand DNA. The result of this process is a double-stranded DNA molecule with additional redundancies at both ends. Note that the DNA genomic structure differs from the RNA genomic structure in having a redundant U3 region added to the 5' end, and a redundant U5 region added to the 3' end. This occurs because the reverse translation process copies more than one full length of the RNA genome. Note also that this genomic structure now resembles a normal gene, with U3 being the promoter, with structural genes in the center, and a U5 tail.

The exact process of how the DNA virus inserts into host chromosomes is not known. It is known that the DNA virus first becomes a circle, and that this involves the short inverted repeat sequences at the ends of the virus. These inverted repeats may be involved in some form of DNA hybridization which brings the ends of the virus together, allowing circularization. Subsequently, insertion into the chromosome is generally assumed to be mediated by an enzyme which recognizes the splice site in the circle and directs insertion of a single copy of the virus into a random site within the host chromosome.

The transcription of viral DNA from the DNA pro-virus within a chromosome occurs in a manner similar to the transcription of any host gene. The U3 region functions as a polymerase II promoter and transcription begins at the beginning of the R region. The U3 promoter, like eukaryotic promoters, generally requires a transcriptional activator protein, which turns the promoter "on". Transcription proceeds through most of the provirus and is terminated at the end of the 3' R region. As a results the transcript is a recreation of the smaller and infectious single-strand RNA genome. A poly-A tail is attached to the 3' end of this RNA and the 5' end is capped, making this molecule similar to normal host messenger RNA.

The RNA which is transcribed from DNA can be directly translated into protein, like any mRNA within the host. The GAG and Pol proteins are produced in this way and are subsequently cleaved into several smaller proteins involved in viral assembly and reproduction. In such a case, the 5' end of the RNA binds to a ribosome and protein translation beings at the first AUG codon initiation triplet of the coding sequence closest to the 5' end of the RNA molecule. Translation is terminated by one of the standard "stop" codons. Genes which are distant from the 5' end of the viral RNA cannot be directly translated because of the intervening genes, such as GAG. Such intervening genes can be removed by a splicing process which involves breaks at specific sites in the RNA molecule, and re-ligation of the appropriate pieces. In this case, the 5' end of the RNA molecule is unchanged, and binds to the ribosome as before, but now the first AUG codon where translation begins is not at the beginning of the GAG sequence, but at the beginning of some other coding sequence further downstream.

Some viral RNA is not translated into protein but rather is packaged into infectious viral particles. Such packaging involves the binding of certain viral proteins to specific sequences of the viral genome. For examples in the RSV viral system, it is part of the GAG sequence which is one of the parts of the genome which binds to and is recognized by such proteins and have been shown to be necessary for packaging of the RNA. The RNA which is packaged into viral particles does not appear to be reverse-transcription-competent until "maturation" of the particle, i.e., after it has existed away from the host cell.

All retroviruses, including HIV, once inserted into the host chromosome, must have their genes translated into viral proteins. If viral proteins are not abundants the retrovirus cannot efficiently propagate to other cells and is not cytopathic to the infected host cell (Dayton et al., *Cell*, 44:941–947, 1986); Fisher et al., *Nature*, 320:367–371, 1986). Such proteins are not produced without the proper functioning of certain viral regulatory proteins. One of the key DNA/RNA-binding regulatory proteins for the retrovirus HIV is the TAT protein (Keegan et al., *Sciences* 231:699–704, 1986). The TAT protein is essential to protein translation of HIV, and possibly also involved in RNA transcription. It is apparent that the TAT protein recognizes and binds to the nucleic acid sequence corresponding to the 5' end of the R region. A second activator gene ART has also been shown to be important in HIV translation (Sodroski et al., *Nature*, 321:412–417, 1986). DNA/RNA binding of the previously described activator proteins is essential to HIV replication. Therefore, introducing genes into host cells, i.e., somatic gene therapy for humans or other mammals, or germline transformation for animals, which will code for modified proteins of the retrovirus which compete or interfere with TAT or ART, will effectively block retrovirus replication.

Past research efforts have been predominantly confined to two traditional anti-retroviral approaches: immunological prevention and pharmacological therapy. Unfortunately, neither of these approaches appears to be very promising for control of retrovirus diseases. At best, an effective vaccination might reduce risk of infection in healthy individuals, but it would not be expected to cure an infected individual. Also, chemical repression of virus diseases has not generally been effective in eradicating any persistent virus, and certainly would not be expected to eradicate a retrovirus. Anti-viral chemicals tend to slow the progress of a virus and to bolster native defense mechanisms, but chemical treatments must be continuously applied and typically have undesirable side effects.

For these reasons, it is doubtful that any retroviral disease can be cured by the traditional anti-viral approaches. An alternative approach to inhibiting retrovirus replication is genetic inhibition by introducing nucleic acid constructs into host cells, i.e., somatic gene therapy or germline transformation, which will confer cellular resistance by hybridization interference.

The inhibition or modulation of the various steps in the retroviral replication process by DNA or RNA which will hybridize and block viral sequences has been termed "hybridization interference" (Green et al., *Ann. Rev. Biochem.*, 55:569–97, 1987), which is incorporated herein by reference. There are essential steps in retrovirus replication which require nucleic acid hybridization (Gilboa et al., *Cell*, 6:93–100, 1979). If any of these replication steps are blocked by pre-binding of the essential sites in the retrovirus genome; or binding of proteins or other cellular constituents in the retrovirus genome, to molecules coded for by genetically engineered nucleic acid sequences in the host cell the retrovirus replication process can not proceed. Note, that "Hybridization Interference" has also been referred to as an "Anti-sense approach" (Green et al., supra). However, an ambiguity exists in that "sense" and "anti-sense" only apply to sequences coding for proteins, and nucleic acid constructs are disclosed herein which target retrovirus sequences not coding for proteins. Consequently, as used throughout the specification and appended claims, "Hybridization Interference" or "Anti-sense RNA" should refer to the use of RNA or DNA to bind with nucleic acid, protein or other cellular constituents to inhibit retrovirus replication.

The effectiveness of the anti-sense RNA approach has been demonstrated in several model viral systems. It was demonstrated in the SP bacteriophage system that certain messenger-RNA-interfering complementary RNA (micRNA) can have very significant anti-viral effects, as seen by reduced plaque number and plaque size (Coleman et al., *Nature*, 315:601–603, 1985).

In addition, it has been suggested that the replication and cell transformation of the Rous Sarcoma Virus (RSV) was inhibited by a specific synthetic tridecamer oligodeoxynucleotide (Zamecnik and Stephenson, *Proc. Natl. Acad. Sci.*, 75:280–288, 1978). The synthetic complementary tridecamer was introduced extracellularly into the cytoplasm of chick embryo fibroblast cells infected with RSV virus, thereby blocking RSV replication by hybridization competition. However the tridecamer was not incorporated into the host genome or any other genetic vehicle, such that neither the sequence, nor an equivalent coding sequence, would replicate in the cell. This is a chemotherapeutic approach to inhibiting virus replication, and not gene therapy.

Another publication has shown that synthetic exogenous oligodeoxynucleotides complementary to regions of the HIV genome inhibit virus replication and gene expression in cultured cells. Sequences of exogenous synthetic oligodeoxynucleotides 12, 20, and 26 nucleotides in length were tested on infected cells (Zamecnik et al., *Proc. Natl. Acad. Sci.*, 83:4143–4146, 1986). Again, the oligodeoxynucleotides are exogenous and were not incorporated into the host genome or another vehicle which would provide for the replication or maintenance of the tridecamer.

Finally, the anti-sense RNA-mediated inhibition on the replication of arian retrovirus in cultured cells was suggested using natural gene sequences derived from the neomycin resistant gene of the bacterial transposable element Tn5 (To et al., *Molecular and Cellular Biology*, 6:4758–4762, 1986).

In the field of human medicine, altering the genotype of the host has not been a desirable method of fighting infectious disease. However, it is now believed that gene therapy will be possible in the relative future (Anderson, *Science*, 226:401–409, 1984). As a result, application of the anti-sense RNA approach within the field of medicine may be possible. Presently available gene therapy techniques are only effective for the genetic modification of bone marrow and blood cells. Because of this limitation, the projected use of gene therapy has generally been assumed limited to the correction of rare hereditary gene defects where such defects center in bone marrow or blood cells. Despite these limitations there are certain pathogens of the blood for which conventional defenses appear inadequate, and where the use of anti-sense RNA inhibition might be feasible. Many of the cells that are infected by retroviruses are derived from hematopoietic stem cells. If these stem cells can be altered by the incorporation of genes or other nucleic acid sequences which will synthesize RNA molecules that are antagonistic to virus propagation, an efficient method to both effectively prevent and to treat these retroviral diseases will be apparent. Further, if the expression of the RNA inhibiting genes can be regulated in the desired cells, it has application to other genetic diseases.

It would therefore be desirable to provide methods and compositions for producing RNA which is complementary to an essential retroviral hybridization site within the retrovirus genome selected from the group consisting of the LTR region, the U5 region, the U3 region, the R region, the PBS region, the AUG start codon regions, the polyp region, RNA splice sites, the leader region, the TAT splice site, the ART splice site and the cap site which would be effective to inhibit one or more steps of the retroviral infection process.

Another objective is to provide methods and compositions for expression in a host cell system of a synthetic double-strand DNA fragment coding for an RNA fragment complementary to an essential retroviral hybridization site within the retrovirus genome selected from the group consisting of the LTR region, the U5 region the U3 region, the R region, the PBS region, the AUG start codon regions, the polyP region, RNA splice sites, the leader region, the TAT splice site, the ART splice site and the cap site, without adverse side effects to the host cell resulting from such gene expression.

SUMMARY OF THE INVENTION

In accordance with the present invention, a method of conferring genetic resistance to retroviral infection upon a host cell is disclosed. The method involves transforming the host cell with a vector comprising a polynucleotide directing transcription within the host cell of RNA which (a) is complementary to a nucleic acid sequence within one or more regions within the genome of the retrovirus selected from the group consisting of the LTR region, the U5 region, the U3 region, the R region, the PBS region, the AUG start codon regions, the polyP region, RNA splice sites, the leader region, the TAT splice site, the ART splice site and the cap site, and (b) confers resistance to retroviral infection upon a host cell by inhibiting in the infection process at least one step of the process selected from the group consisting of retroviral replication, reverse transcription, and translation. The method also involves transforming the host cell with a vector comprising a polynucleotide directing transcription within the host cell of RNA which corresponds to sequences which represent a small, functional portion of the RNA genome, which can bind to a viral protein.

Cells upon which resistance to infection is to be conferred, are transformed with a polynucleotide via a vector. "Transformation" or "transformed", as those terms are used throughout this specification and the appended claims, is intended to cover any and all methods of introducing a polynucleotide and its other attendant nucleic acid sequences, if any, into a cell. Those terms are not intended to be limited to the process of "true" transformation which is known to those in the art. Methods included within those terms include, without limitation, transformation, transfection, microinjection, CaPO$_4$ precipitation, electroporation, targeted liposomes, particle-gun bombardment, electro-fusion, and infection.

The polynucleotide used to transform the cell upon which resistance is conferred can be either single- or double-stranded RNA or DNA. The polynucleotide "directs" transcription of a specific RNA molecule in the cell. A polynucleotide can "direct" such transcription by being directly transcribed (e.g., double-stranded DNA in a plasmid) or by coding for nucleic acid which is later transcribed to produce the RNA molecule (i.e., serves as a template for RNA or DNA which is either transcribed or serves as a further template for nucleic acid which is transcribed; e.g., single-stranded RNA in a virus which is transcribed to produce DNA which is incorporated into the host cell genome and in turn transcribed). In addition to the sequence specifically directing the transcription of the operative RNA, the polynucleotide can include a promoter and/or a terminator that will regulate the transcription of the polynucleotide. The polynucleotide may be derived from a naturally-occurring sequence or synthesized in vitro.

Used herein, an RNA molecule is complementary (antisense) to a given nucleic acid sequence if it will effectively bind or hybridize to any portion of the given nucleic acid sequence, wherein here the nucleic acid sequence as an essential hybridization site within the retroviral genome so as to inhibit a process involved in retroviral replication. Similarly, an RNA molecule is corresponding (sense) to a certain nucleic acid sequence if it will bind to any portion of a nucleic acid which is complementary, as defined above, to the certain nucleic acid sequence so as to produce inhibition of retroviral replication, reverse transcription, or translation. No specific degree or percentage of complementarity (as the term is traditionally used in the art), base-to-base pairing, homology (as that term is traditionally used in the art), or base-to-base comparison is required.

The RNA directed by the polynucleotide is complementary to "one or more" of certain regions within the retroviral genome. In other words, the RNA may overlap between several regions or portions of regions; or the polynucleotide can direct transcription of RNA at several different sites.

The RNA directed by the polynucleotide must be effective to inhibit at least one step of the retroviral infection process. Inhibition can be exhibited by any decrease in the extent or rate of insertion and/or proliferation of the retrovirus. Replication need not be completely stopped to constitute "inhibition."

The polynucleotide may be introduced into a host cell as part of a vector. Any known vectors, including without limitation, viral vectors, retroviral vectors and plasmids, may be used. Preferably the vector is a plasmid. The vector can include a promoter and/or a terminator for regulation of the polynucleotide. The final construct (vector and polynucleotide) can include one or more promoters and/or terminators including those made part of the polynucleotide as described above. The vector can also include a selectable marker for detection and isolation of successfully transformed cells including without limitation antibiotic resistance to neomycin, ampicillin, or xanthine.

The present invention is applicable to any retrovirus, including without limitation a human T-cell lymphotrophic virus, a human immunodeficiency virus, a feline immunodeficiency virus (FIV), a lymphadenopathic virus, a leukemia virus, a sarcoma virus, and a virus causing a lymphotrophic disease. Such viruses include without limitation HIV, FIV, feline leukemia virus ("FeLV"), HTLV-I, HTLV-II, murine leukemia virus and avian leukemia virus. Preferably the retrovirus is HIV, HTLV-I, FeLV, or FIV.

Nucleic acid constructs, including a polynucleotide as previously described, are also disclosed. The construct can include a vector as previously described.

Resistance to retroviral infection is conferred to host cells by hybridization interference, or by modified viral proteins. "Hybridization" is the coming together of single-stranded nucleic acid chains with their complementary nucleotide sequences into double-stranded nucleic acid chains when subjected to hybridizing conditions. "Hybridization Interference" is the inhibition of viral replication by "hybridization" of interfering nucleic acid sequences.

Cells upon which resistance to infection has been conferred by the above-described methods and their progeny are also disclosed. The progeny of the originally transformed cells "contain a sequence which is descendant from" the polynucleotide previously described. A sequence is "descendant" if its history can be traced back to the polynucleotide. The descendant sequence does not have to be an exact copy of the polynucleotide; it need only maintain the function of the polynucleotide in the inhibition process. In essence, a "descendant sequence" must correspond (as defined above) to the polynucleotide. The descendant sequence can have been deleted, inserted, mutated, inverted or altered by other means as long as its functional identity with the polynucleotide is maintained.

RNA molecules directed by the polynucleotide are also disclosed. Such molecules are (a) complementary to a nucleic acid sequence within the genome of a retrovirus, and (b) effective to inhibit at least one step of the retroviral infection process.

A method of treatment is disclosed in which cells, upon which resistance to infection has been conferred, are introduced into a patient.

DETAILED DESCRIPTION OF THE INVENTION

Figure 1:
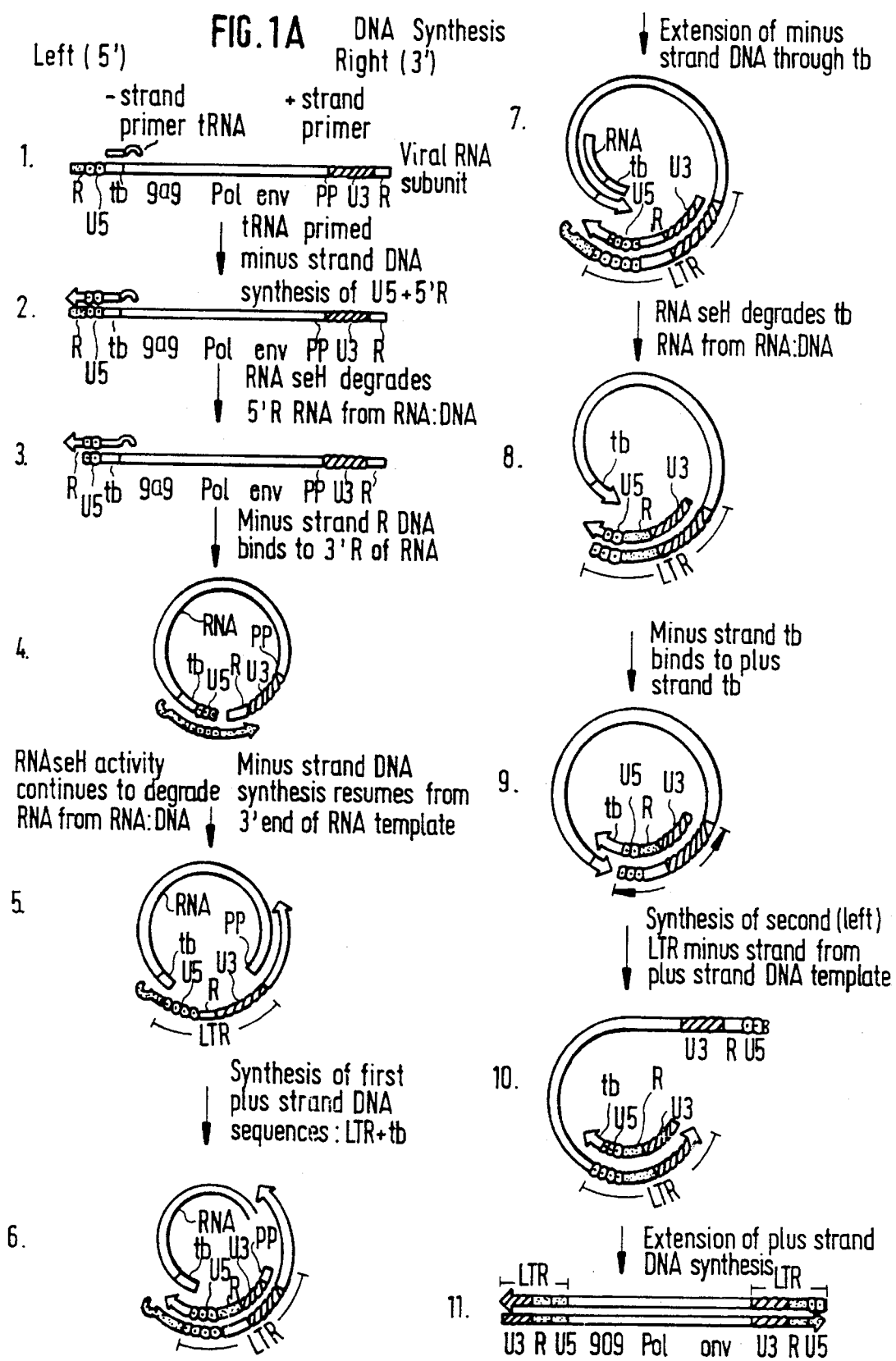
FIG. 1A is a schematic representation summarizing a model of the synthesis of a double-strand DNA from viral RNA.
FIG. 1B is a schematic representation showing a general overview of a retrovirus life cycle.
Figure 2:
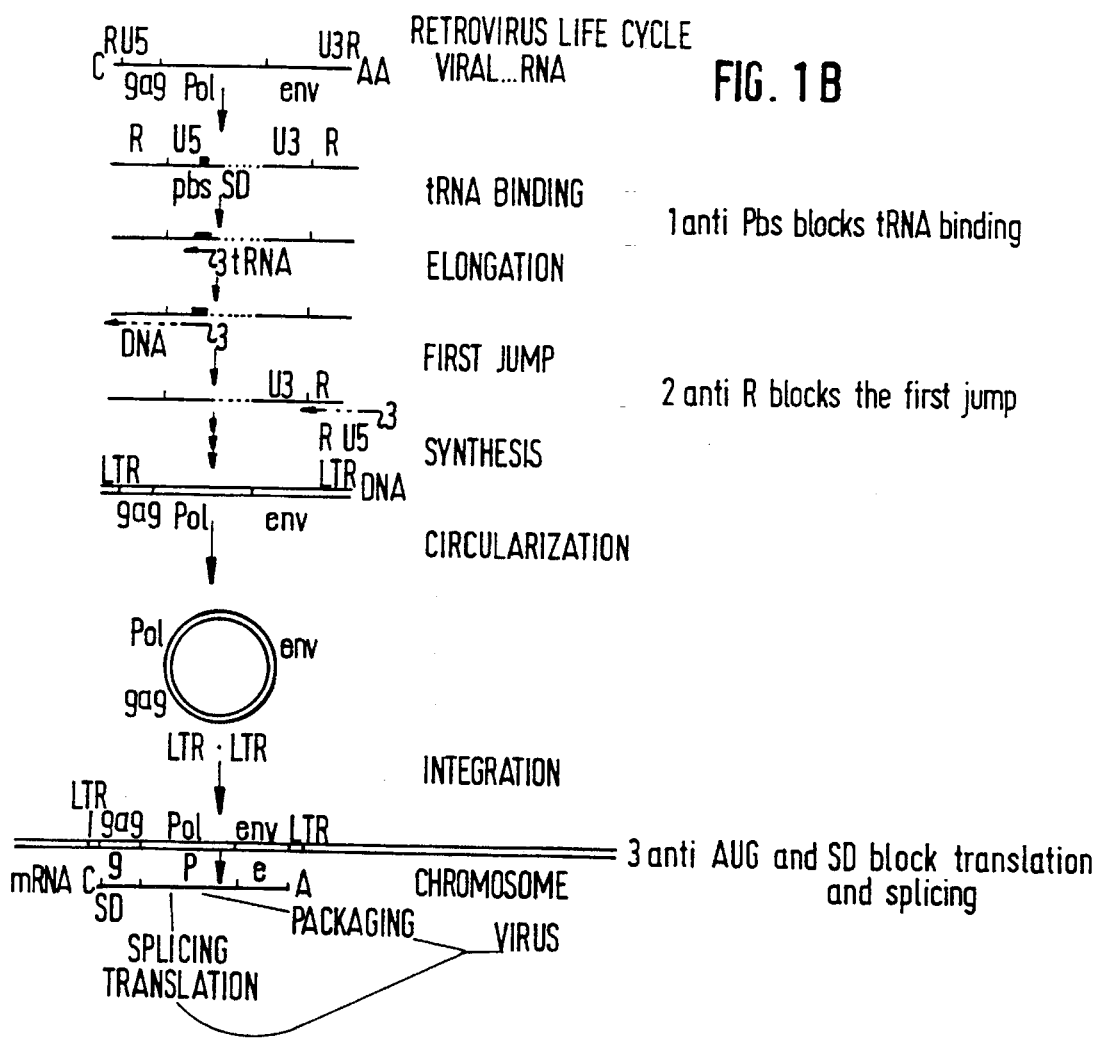
FIG. 2 is a comparison between Murine Leukemia Virus (MLV) and Feline Leukemia Virus (FeLV) LTR regions showing sequence similarities indicated by the underlined nucleotide sequences.

Many of the procedures useful for practicing the present invention, whether or not described herein in detail, are well known to those skilled in the art of Recombinant DNA technology. A detailed description of many of such procedures can be found in Maniatis et al. (*Molecular Cloning: A Laboratory Manual,* Cold Spring Harbor Laboratory, Cold Spring Harbor, N.Y., 1982).

The present invention specifically involves the inhibition of at least one step of the retroviral infection process by RNA complementary or corresponding to a site within the retroviral genome essential for replication, reverse transcription, translation or viral assembly. In the following examples, the methods of the present invention are applied to HIV and FIV viruses for purposes of illustration of the invention taught herein and are not limited thereto. The nucleic acid sequences of the Long Terminal Repeat region of HIV, FIV, and HTLV-I are shown in SEQ ID NOs. 1, 2 and 3, respectively. Table 1 lists several sequences which are exemplary of the polynucleotides employed in practicing the present invention. Use of these sequences is not limited to the HIV virus but can apply in accordance with the methods described herein to all retroviruses, although some changes in specific bases within the polynucleotide may be required. The genetic code is degenerate and redundant, that is, numerous substitutions, deletions, inversions or insertions of nucleotides will code for the same end product, i.e., protein. Consequently, it will be apparent that any changes or modifications to a given polynucleotide that produce a new polynucleotide that retains sufficient functional sequence identity to hybridize to, or compete with, targeted nucleic acid sequences within the retroviral genome so as to inhibit at least one step in the process of retroviral infection, are functional equivalents of specific sequences disclosed herein.

The term "nucleic acid construct" as used herein, refers to one or more nucleotide sequences (polynucleotides) that are inserted into one of the vectors chosen from the group of vectors including a virus, retrovirus, or plasmid. The polynucleotide sequences described herein are preferably DNA, but could include RNA or a combination thereof, and are integrated into the appropriate vector by ligation or other similar techniques. With reference to Table 1, there are listed sequences which are illustrative of the polynucleotides of the nucleic acid constructs which are inserted into the appropriate vector.

TABLE 1

| Anti-HIV Sequence name | Anti-HIV Sequence | HIV target site | Modes of Action |
|---|---|---|---|
| 1. Anti-R | 1–97 (minus strand) | 5'R-region of viral RNA and of mRNA | Block "1st jump" of reverse transcription TAT binding and translation of mRNA |
| 2. R homolog | 1–97 (plus strand) | 3'R-region of minus strand cDNA | Block "1st jump" of reverse transcription |
| 3. Anti-PBS | 170–210 (minus strand) | PBS site of viral RNA and of plus strand cDNA | Block initiation of reverse transcription and "2nd jump" |
| 4. PBS homolog | 182–199 (plus strand) | 3'PBS region of minus strand cDNA | Block "2nd jump" of reverse transcription |
| 5. False primer | Lys TRNA (with 3' 18 bp substitution) | Any new PBS site of viral RNA | Initiate reverse transcription at improper site |
| 6. False template | PBS homolog (with 5' false tail) | Primer complex and secondary site | "Disarm" primers, produce anti-viral cDNA |
| 7. Polypurine homolog | 8630–8670 (plus strand) | Polypurine complement in minus strand cDNA | Block proper initiation of plus strand DNA synthesis |
| 8. Anti-S | 270–340 (minus strand) | Acceptor site for 1st TAT splice and GAG initiation codon of mRNA | Block splicing needed for TAT translation and initiation of GAG translation |
| 9. Anti-TATS | 5340–5430 (minus strand) | Donor site for 1st TAT splice and TAT initiation codon of mRNA | Block splicing needed for TAT translation and initiation of TAT translation |
| 10. Anti-TATS | 5610–5640 (minus strand) | Acceptor site for 2nd TAT splice of mRNA | Block mRNA splicing needed for TAT translation |
| 11. Anti-TATS | 7940–7970 (minus strand) | Donor site for 2nd TAT splice of mRNA | Block of mRNA splicing needed for TAT translation |
| 12. TAT repressor | 5530–5593 (plus strand) | 5'end of mRNA | Block binding of TAT activator |
| 13. ART repressor | 7956–8080 (plus strand) | ART binding site of mRNA | Block binding of ART activator |

Also with reference to SEQ ID NOs. 1–23, there are listed sequences which are illustrative of the polynucleotides of the nucleic acid constructs which can be inserted into the appropriate vector in accordance with the present invention.

EXAMPLE 1

Production of Nucleic Acid Constructs

Novel nucleic acid constructs, in accordance with the present invention, may be produced by cloning a polynucleotide into a vector, wherein the double-stranded DNA oligonucleotide sequence comprising the polynucleotide is operatively associated with a strong promoter and a corresponding terminator sequence. The promoter and terminator sequence, such as a Pol III promoter and terminator, may be included in the synthesis of the polynucleotide; or alternatively, the promoter and terminator are part of the parent vector such that when the polynucleotide is inserted in the proper orientation in relation to the promoter and terminator, it becomes operatively associated therewith. Transcription of the nucleic acid construct results in a RNA molecule complementary (anti-sense) to one or more sequences within the retroviral genome which is an essential hybridization site involved in a process comprising retroviral replication, reverse transcription, or translation. The sequence, targeted within the retroviral genome, includes the LTR, the AUG start codon regions, RNA splice sites, the U5 region, the U3 region, the PBS region, the cap site, the TAT splice site, the ART (now called REV) splice site, the leader region, and the polyP region.

The present invention also is directed to a nucleic acid construct, which when transcribed, results in RNA which corresponds in sequence (sense) to a small, functional portion of the retroviral genome. The sequence in the retroviral genome, such as initiation sites for reverse transcription (ex. the R region and PBS region), are involved in binding to a viral protein, retroviral reverse transcriptase, in an essential viral process. Thus, corresponding RNA, produced in accordance with the present invention, can compete with the genomic sequence, for binding with the viral protein.

Oligonucleotides comprising the polynucleotides can be synthesized using an automated DNA synthesizer, as previously described in copending application Serial No. 739,718, now U.S. Pat. No. 5,324,643. Alternatively, oligonucleotides comprising the polynucleotides may be synthesized by DNA amplification using methods commercially available. For example, the polymerase chain reaction has been used to synthesize polynucleotides. Primers are hybridized to opposite strands of a segment of the proviral DNA containing the sequence to be amplified. The temperature is then raised to permit replication of the specific segment of DNA across the region between the two primers by a thermostable DNA polymerase. Then the reaction is thermocycled so that at each cycle the amount of DNA representing the sequences between the two primers is doubled, and the DNA is further amplified. Purification of the amplified sequence, comprising the polynucleotide, can be accomplished using any one of several methods known in the art including electrophoresis, or methods utilizing DNA-binding beads or matrices. The polynucleotides can be synthesized so that they further comprise flanking restriction sites at the 5' and 3' ends to facilitate cloning into a vector that has the same or compatible restriction sites. The polynucleotides used in the nucleic acid constructs are of sufficient length to insure that the RNA transcribed therefrom is stable and prevents degradation by host cell enzymes; and yet are limited in length so as to reduce the problem of the formation of tertiary structures associated with lengthy RNA molecules which tend to fold or "hairpin" thus preventing binding of the RNA to the essential hybridization site of the retroviral genome.

Figure 3:
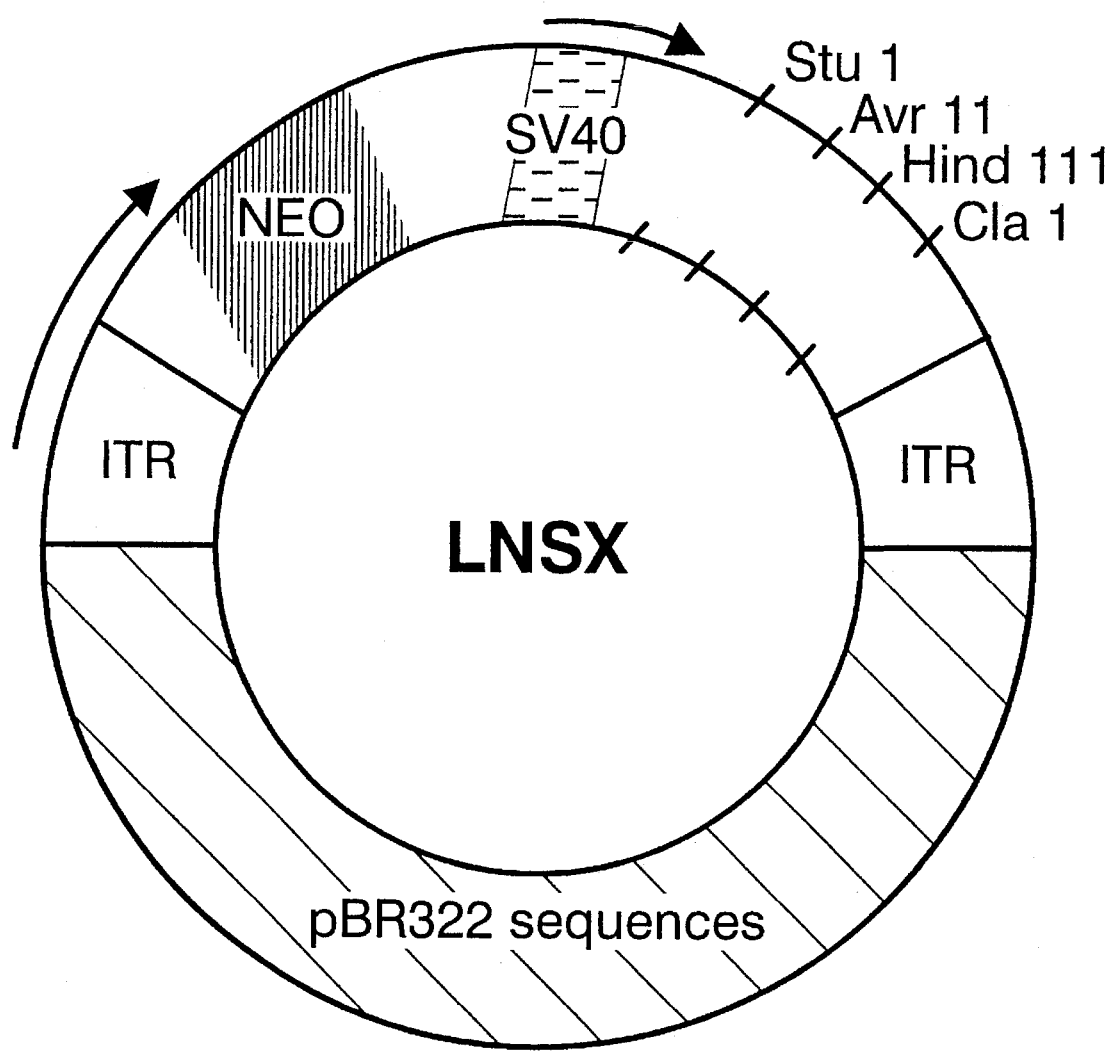
FIG. 3 is a schematic representation of the AAV vector used as an illustration of the nucleic acid constructs of the present invention.

Vectors, used in accordance with the present invention as a vehicle for introducing into the host cell and expressing the polynucleotide incorporated therein, can be selected from plasmids, viruses, and retroviruses. The features of a vector which make it useful in the methods of the present invention include that it have a selection marker for identifying host cells which have been transfected by the vector; and restriction sites to facilitate cloning of the polynucleotide insert in forming the nucleic acid construct (recombinant vector). Examples of useful vectors include, but are not limited to, plasmids pRSVneo, pSV2gpt, and pSV2neo. A retroviral vector, such as a plasmid containing AAV (Adeno-associated virus) sequences, is also useful (see for example Chatterjee et al., 1992, *Science*, 258:1485–1488). A preferred AAV vector, LNSX, is derived from the single-stranded AAV virus which has inverted terminal repeats (ITR) flanking genes encoding viral proteins. During the initial construction of AAV vector LNSX, these genes are removed, and the ITRs are included with a selection marker such as the gene encoding neomycin resistance, an SV40 promoter, a polylinker, and with sequences from pBR322 (FIG. 3). A promoter in the ITR drives the expression of the neomycin phosphotransferase gene, whereas the SV40 promoter drives expression of sequences, such as anti-sense, inserted in the polylinker. The inverted terminal repeats of the AAV vector provide a means for integrating the vector, and sequences inserted therein, into the chromosome as the repeats serve as a sequence which has been shown to insert site-specifically, rather than randomly, into chromosomes.

EXAMPLE 2

In this illustrative embodiment of the present invention, plasmids were constructed which were capable of expressing an anti-sense transcript to the FIV LTR region and the primer binding site (PBS) of FIV. Plasmids were also constructed to express a sense transcript to these FIV regions. A polynucleotide corresponding to these FIV regions was synthesized by using the polymerase chain reaction using the following primers: the forward primer- ATC AAG CTT CTT GCT AAT GAC GTA TAA GT (SEQ ID NO. 24); the reverse primer- ATC AAG CTT AGC AGG AGT TCT GCT TAA (CA (SEQ ID NO. 25). The polynucleotide, comprising 289 bases illustrated in SEQ ID NO. 2, was synthesized to include flanking HindIII restriction sites. The polynucleotide was digested with HindIII, and then ligated to AAV plasmid vector LNSX, previously digested with HindIII, in forming the nucleic acid constructs. The resultant constructs were then used to transform *Escherichia coli* strain DH5α. Recombinant plasmids contained within the transformants were isolated and screened for the orientation of insertion of the polynucleotide into the plasmid using restriction enzyme digestion and agarose gel electrophoresis, and confirmed by dideoxy sequence analysis. Plasmid clones AS6.8, AS4.1 and AS3.8 contain the polynucleotide comprising the LTR and PBS regions in the anti-sense orientation; whereas plasmid clone S6.8 contains the LTR and PBS regions in the sense orientation.

The calcium phosphate precipitation method was used to introduce each of the nucleic acid constructs individually into feline cell lines. Following transfection, cells were maintained for 24 hours in cell growth mediums to allow expression of resistance to neomycin, before being transferred in cell growth medium containing 800 μg/ml G418 which was used for selection. Following selection, cells were maintained in growth medium containing 600 μg/ml G418.

To evaluate whether resistance to FIV infection was conferred on cells containing the nucleic acid construct, cells of feline lymphocyte cell line 3201 were transfected one of the nucleic acid constructs, which when transcribed would result in the production of complementary or anti-sense (AS6.8, AS4.1 AS3.8) RNA to the FIV LTR region and the PBS. Also, cells were transfected with the AAV vector without inserts which served as a control (designated "WT"). The transfected feline cells were challenged with the feline petaluma isolate of FIV at a multiplicity of 5 to 10 $TCID_{50}$. Cells were maintained in medium without G418 during the FIV challenge, and the challenged cells were monitored for virus production by measuring reverse transcriptase released into the medium. Reverse transcriptase was measured using poly(ra): oligo(dt) as a template primer, as described previously by Heine et al.(1980, *J. Gen. Virol.* 49:385).

Figure 4:
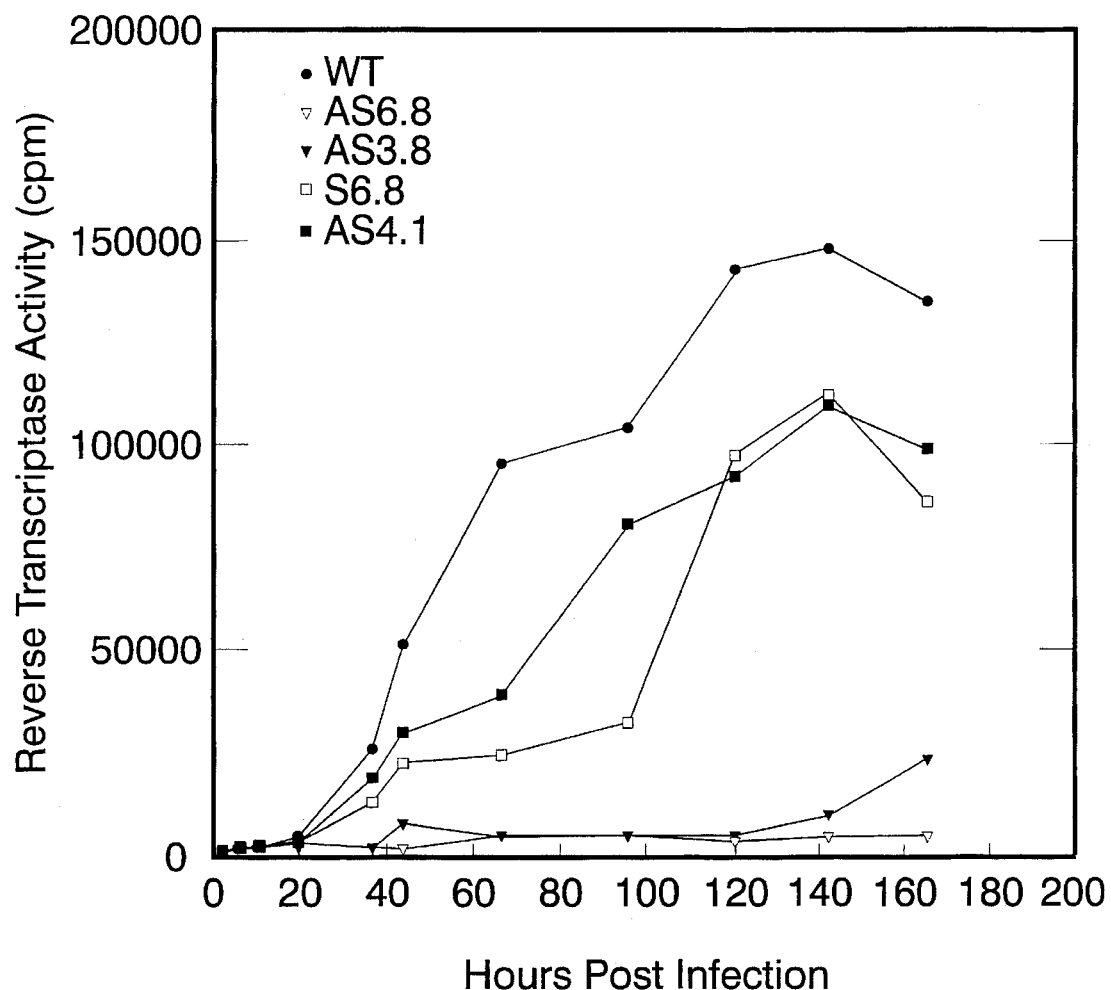
FIG. 4 is a graph showing reverse transcriptase activity of FIV-infected cells.

Upon stably transfecting the feline lymphocyte cell line with a vector expressing anti-sense transcripts specific for the 5'LTR and the primer binding site in the FIV genome, anti-sense mediated inhibition of FIV infection was demonstrated. No detectable reverse transcriptase activity (FIG. 4, ∇, ▼) could be demonstrated for over 120 hours post-infection for cells transfected with AS6.8 and AS3.8. Some decrease in reverse transcriptase activity was observed in cells transfected with AS4.1 (FIG. 4, ■) when compared to control cells (FIG. 4, ●). Because no reverse transcriptase activity was observed for some time in the cells transfected with constructs AS6.8 and AS3.8 encoding anti-sense RNA to the LTR region and the PBS region, it can be concluded that inhibition of the FIV infection process involved blocking the initiation of reverse transcription (anti-PBS), and translation (anti-LTR).

EXAMPLE 3

In this illustrative embodiment of the present invention, plasmids were constructed which were capable of expressing an anti-sense transcript to the HIV LTR region, and the primer binding site (PBS) of HIV. Plasmids were also constructed to express a sense transcript to these HIV regions. A polynucleotide corresponding to these HIV regions was synthesized by using the polymerase chain reaction using the following primers: the forward primer- ATC AAG CTT ATC GAG CTT GCT ACA AGG GA (SEQ ID NO. 26); the reverse primer- ATC AAG CTT CTG CGT CGA GAG AGC TCT G (SEQ ID NO. 27). The polynucleotide, comprising 355 bases illustrated in SEQ ID NO. 1, was synthesized to include flanking HindIII restriction sites. The polynucleotide was digested with HindIII, and then ligated to AAV plasmid vector LNSX, previously digested with HindIII, in forming the nucleic acid constructs. The resultant constructs were then used to transform *Escherichia coli* strain DH5α. Recombinant plasmids contained within the transformants were isolated and screened for the orientation of insertion of the polynucleotide into the plasmid using restriction enzyme digestion and agarose gel electrophoresis; and confirmed by dideoxy sequence analysis. Plasmid clone pHIV12 contained the polynucleotide comprising the LTR and PBS regions in the anti-sense orientation; whereas plasmid clone pHIV21 contained the LTR and PBS regions in the sense orientation.

Electroporation was used to introduce each of the nucleic acid constructs individually into human cell lines H9; HUT 78, and CEM. Following electroporation at 400 volts, cells were maintained in flasks for 6 days in cell growth medium, to allow expression of resistance to neomycin, before being transferred in cell growth medium containing 800 μg/ml G418 which was used for selection. Following selection, cells were maintained in growth medium containing 600 μg/ml G418.

To evaluate whether resistance to HIV infection was conferred on cells containing the nucleic acid construct, cells of human lymphocyte cell line CEM were electroporated with the nucleic acid construct, which when transcribed would result in the production of complementary or anti-sense (pHIV12) RNA to the HIV LTR region and the PBS region. The electroporated human cells were challenged with the BP-1 isolate of HIV. Also, as a control, human cells not containing the nucleic acid construct were challenged. Virus, used for the challenges, was obtained from an infected, continuously growing cell line by harvesting culture supernatants which were aliquoted and stored at −70° C. until just prior to use. For viral challenges, 500,000 viable CEM cells were washed with media, and dilutions of the virus-containing culture supernatant were added. Cells were incubated in the virus-containing culture supernatant for 60 minutes at 37° C. to allow for virus infection, and then the cells were washed to remove virus that had not penetrated cells. The challenged cells were monitored for virus production by culturing them for 4 days post-challenge, harvesting the culture supernatant, and assaying the culture supernatant using a commercial HIV P24 antigen ELISA kit (Cellular Products, Inc.) in accordance with the directions of the manufacturer. P24 antigen concentration is expressed in pg/ml.

Figure 5:
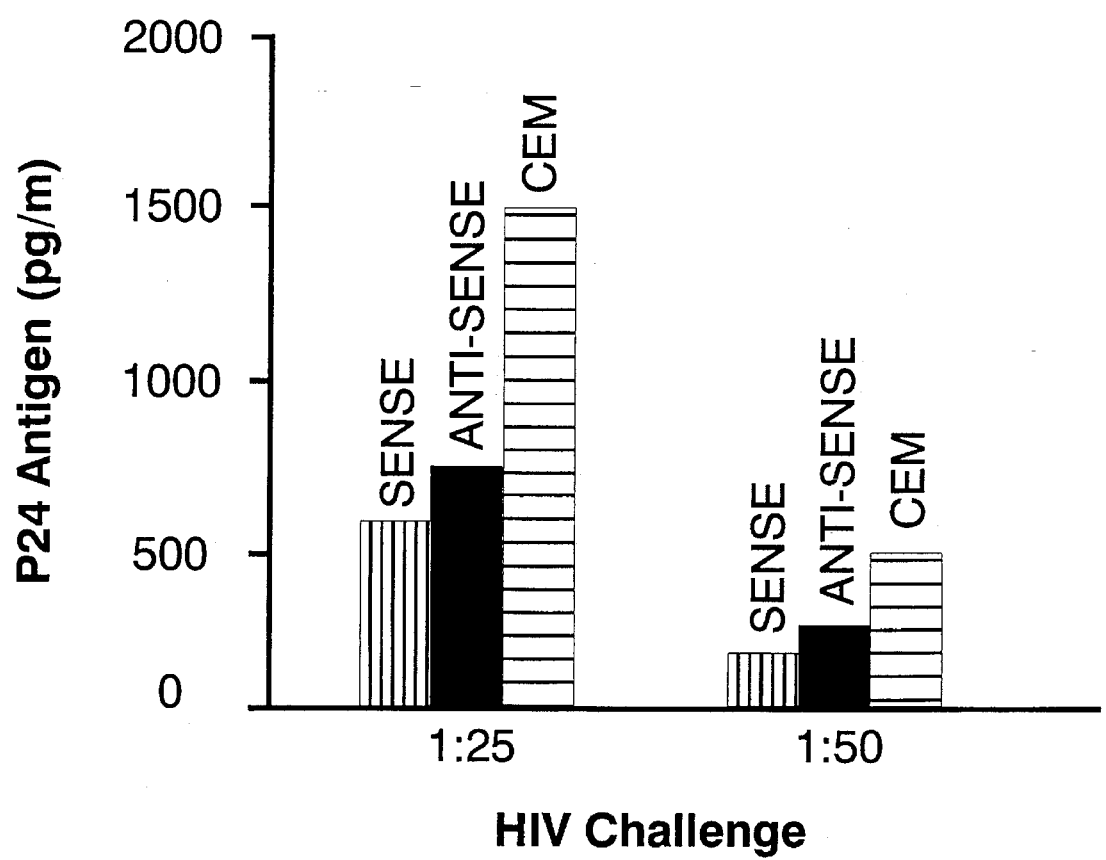
FIG. 5 is a bar graph showing P24 antigen detection measured for HIV-infected cells.

Upon stably transfecting the human lymphocyte cell line with a vector expressing anti-sense transcripts specific for the 5'LTR and the primer binding site in the HIV genome, anti-sense mediated inhibition of HIV infection was demonstrated. As illustrated in FIG. 5, P24 antigen detection was reduced in CEM cells containing pHIV12 ("ANTISENSE"), when compared to CEM cells without any nucleic acid construct ("CEM"). The reduction in P24 antigen detection was seen with HIV challenges at both a 1:25 dilution and a 1:50 dilution of virus-containing culture supernatant. Anti-sense mediated inhibition of viral infection, as measured by reduction in P24 antigen detection, continued to be observed for greater than 10 days post-transfection.

EXAMPLE 4

Human Bone Marrow Auto-Transplant

This embodiment is in accordance with the procedures and methods described in Example 1 or 2. Auto-transplant of bone marrow (i.e., re-introducing a patient's own bone marrow cells) is now a relatively minor and routine procedure. Bone marrow cells are extracted by syringe, and in the present case, transformed and cultured. The patient is then irradiated, or otherwise treated, to destroy existing bone marrow cells remaining in the patient. Then the transformed cultured bone marrow cells are injected back into the patient's circulatory system. Such cells eventually migrate back into the bone marrow, re-establishing that tissue.

In order to make all of the lymphocytes of a patient immune to the AIDS related virus, bone marrow cells would be transformed with the nucleic acid constructs of the present invention by any of the methods already discussed;

and transformed cells would be selected for. Multiple nucleic acid constructs can be employed. Preferably, the polynucleotide sequence(s) employed in the constructs will direct transcription of RNA complementary to the R region, the primer binding site (PBS) with a false leader and a false primer coding sequence, the first splice region and/or the AUG site. Non-transformed bone marrow within the patient would be destroyed and the transformed bone marrow cells would be used to re-establish the bone marrow tissue. As a result; all lymphocytes, including T4 cells, deriving from the transformed bone marrow would be immune to the virus. Consequently, the virus would be eradicated from the patient's system. It should be noted that irradiation of the patient may not be necessary since the AIDS pathology results in killing of infected cells by the HIV virus itself, thus reducing the infected T4 cell population.

Auto-transplant can be performed in both human and other mammalian, e.g., feline systems using sequences specific for FIV and/or FeLV. In cats, the germline of the animal might be transformed to produce virus resistant strains (breeds) of cats.

EXAMPLE 5

Injection of Nucleic Acid Constructs

Alternatively, transformation can be accomplished in situ by encapsulating constructs of the present invention into liposomes using established methods, binding commercially available antibodies to the surface of the liposomes which specifically bind to T4 cells; and injecting these liposomes into the blood stream of the patient. The antibody-targeted liposomes will bind to T4 cells, and will continually be absorbed by the cell, leading to transformation. Subsequently, transformed T4 cells will have a selective advantage over non-transformed cells, due to their immunity to virus. Such resistant cells will multiply as susceptible cells are killed off by the virus. This selection process can be enhanced by use of selective agents (i.e., antibiotics) favoring the transformed cells. This method would be especially appropriate for AIDS patients who could not tolerate a bone marrow transplant (see above).

This embodiment is in accordance with the procedures and methods described in Example 1, and can utilize multiple genes in multiple copies, with Pol III promoters. Preferably, the polynucleotide sequence(s) employed in the constructs will direct transcription of RNA complementary to the R region, the primer binding site, the first splice site region and/or AUG start codon region.

Figure 6:
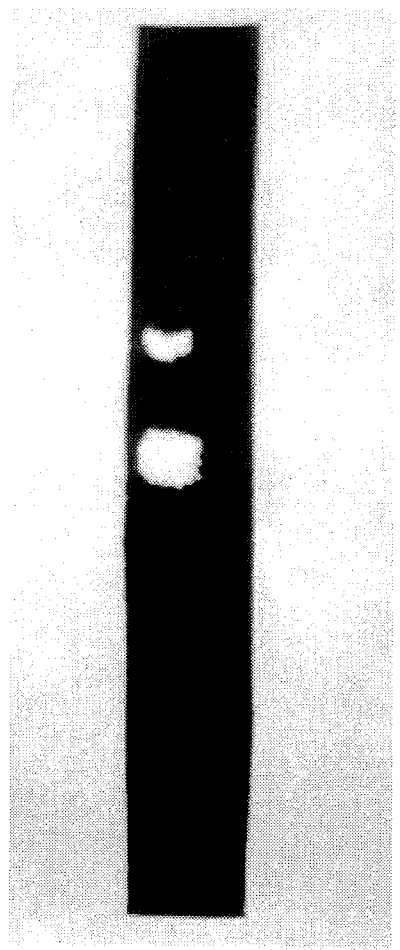
FIG. 6 is a representation showing an agarose gel containing DNA amplified from vector template contained with cat white blood cells.

In another mode of this embodiment, the nucleic acid construct comprising the AAV vector was packaged in AAV capsids, and then the resultant capsids are then injected into the bloodstream as a means of introducing therapy. To illustrate this mode of the embodiment, AAV vector LNSX was co-transfected with a construct encoding AAV viral capsids into cells in vitro such that a virus-like particle is assembled, and LNSX is incorporated via AAV packaging signals contained within LNSX. The virus-like particle was then isolated and injected into the bloodstream of a cat. About two months later, whole blood was drawn from the cat, and DNA was isolated from the white blood cells. The DNA was then subjected to polymerase chain reaction using primers to the neomycin phosphotransferase gene (neo) since neo is a bacterial gene which would not normally be found in the cat's blood cells. As evident in the agarose gel represented in FIG. 6, using a neo-specific primer in amplifying DNA isolated from the blood of the injected cat resulted in an amplified product representing the injected LNSX. Thus, persistence of the injected AAV vector can be demonstrated which suggests that the injected vector inserts and incorporates into the genomic DNA contained within white blood cells.

EXAMPLE 6

Blocking of Reverse Transcription using an Anti-sense RNA Molecule Complementary to the "R" Region This embodiment is in accordance with the procedures and methods described in Example 1. As already described, the R region, found at both ends of the retroviral RNA genome, plays a crucial role in the "first jump" of reverse translation. Reverse transcription becomes stalled at the 5' end of the virus and must be carried to a new template at the 3' end of the virus. This is possible because the enzyme is attached to the cDNA strand which has been transcribed from the 5' R region. This cDNA is naturally complementary to R and can hybridize to the 3' R region. This results in a bridge which circularizes the virus and allows reverse transcription to continue.

This "first jump" can be blocked by an independent RNA molecule which is complementary to the R region. This molecule is transcribed from a construct referred to as "Anti-R". This molecule can hybridize to the 3' R region and will block the 5'–3' bridge from forming between the two ends of the virus. Such hybridization tends to be stable, such that competition for the R hybridization site is on a first-come basis. Since reverse transcription is a particularly slow process, the cDNA molecule transcribed from the 5' end of the virus will not be available until some time after initial cell infection. Therefore, if abundant independent RNA molecules are already present in the cell, and are complementary to R, there will be a very high probability that the R site will be blocked (bound) by them, before the "first jump" is even possible. Consequently, this will preclude successful infection of the cell by that viral strand. Refer to SEQ ID NOs. 4, 6, 7, and 8, for the sequence of the R polynucleotides of HTLV-I, FeLV, HIV, and FIV, respectively.

The R region of retroviruses is the most highly conservative (unchanging) region. However, point mutations do occur in this region. Different R region sequences of different HIV strains show several minor nucleotide differences in this region. Newly arising mutant strains will also have small differences in this region. This is not an important consideration, since nucleic acid hybridization does not require perfect base-pairing. Likewise, the interfering molecule may have additional sequences 5' and 3' or may be less than full length at the R region. The relevant point is that any such novel nucleic acid constructs, as herein described, can direct transcription of complementary RNA that stably hybridize to the R region of the virus, even though base pairing is less than 100%.

EXAMPLE 7

Blocking the Primer Binding Site (PBS) and Adjacent Sequences Using Anti-Sense RNA This embodiment is in accordance with the procedures and methods described in Example 1. This novel nucleic acid construct, when transcribed, produces complementary RNA that can bind to the primer binding site region (hereinafter "Anti-PBS"). As a result, complementary RNA will compete with the tRNA(Lys)/reverse transcriptase samples for this site, thereby blocking initiation of reverse transcription. In addition, the complementary RNA will bind to the double-strand DNA which is involved in the "second jump"

of reverse translation. This will block completion of reverse translation in a similar way as the first two anti-viral molecules. Because of complementation to the 3' end of the U5 region, RNA from this construct may also affect circularization and insertion into the chromosome of the double-stranded viral DNA. Refer to SEQ ID NOs. 9, 10, 11, and 12 for the sequences of the PBS polynucleotides of FeLV, HTLV-I, HIV, and FIV, respectively.

EXAMPLE 8

Anti-Sense RNA Complementary to the Poly-Purine Sequence and Adjacent Sequences

This embodiment is in accordance with the procedures and methods described in Example 1. This novel nucleic acid construct includes the 5' end of the U3 region. The construct, when transcribed, produces RNA complementary to the single-strand DNA, in the region where second strand DNA synthesis begins. If in a RNA form, and if associated with improper flanking sequences, this molecule will bind in the initiation region of second strand DNA synthesis and will block proper synthesis of the double-strand DNA.

EXAMPLE 9

Blocking of the First RNA Splice Site and the First AUG Start Codon Site

This embodiment is in accordance with the procedures and methods described in Example 1. Many RNA molecules must have intervening sequences removed or "spliced out" before they can be properly translated into protein. The HIV virus has at least four "splice" sites. Splicing at such sites is required for translation of several proteins downstream of GAG. Such splicing involves precise recognition of RNA single-stranded sequences by proper enzymes. Nucleic acid constructs, producing complementary RNA capable of hybridizing in such regions, will prevent proper splicing and thereby prevent proper protein translation (herein after "Anti-SD"). Near the same region is the first AUG site, where translation of GAG protein begins. This site is also subject to hybridization interference, since protein translation can not be initiated in a region of double-stranded RNA (herein after "Anti-AUG"). Therefore, complementary RNA molecules spanning these two regions will block translation of GAG protein as well as the other proteins further downstream. Refer to SEQ ID NOs. 13, 14, 15, 16, and 17 for the AUG and S polynucleotide for sequences of FeLV, HTLV-I, and HIV viruses.

As will be seen the RNA molecules already described can be predicted to have additional anti-HIV activity by interfering with additional viral mechanisms. The multi-functional nature of these molecules is important in establishing multiple lines of defense. These are described below:

EXAMPLE 10

Blocking Circulation and Chromosomal Insertion

This embodiment is in accordance with the procedures and methods described in Example 1. The precise mechanisms involved in circularization and chromosomal insertion are unknown, although the 5' and the 3' ends of the virus are obviously involved. The short inverted repeats at these ends presumably allow end-to-end hybridization. It is noteworthy that certain complementary nucleic acid constructs described herein include the inverted repeat at the 5' end of the DNA virus, and the inverted repeat at the 3' end of the DNA virus. Therefore, nucleic acid constructs already described provide potential interfering mechanisms for the viral insertion processes.

EXAMPLE 11

Blocking DNA Transcription/Translation

This embodiment is in accordance with the procedures and methods described in Example 1. Some retroviruses, like HIV, have a specific open reading frame which codes for a transcriptional activator TAT protein. In the absence of this protein, the pro-virus is not transcribed and/or translated (has been controversial), and all viral activities cease. Translation of this protein will be blocked by previously described nucleic acid constructs. Specifically, the Anti-SD and the Anti-AUG nucleic acid constructs can be targeted to block synthesis. Consequently nucleic acid constructs already described can be used to block transcription and/or translation by blocking synthesis of the transcriptional activator protein.

EXAMPLE 12

Blocking of the RNA Packaging Site

This embodiment is in accordance with the procedures and methods described in Example 1. A region of the viral RNA that is essential for packaging of the RNA into infectious particles has been shown in other retroviruses to be between the first splice site and the GAG coding region. It appears that this region binds to one of the GAG proteins. This region is included in the region complemented by the Anti-SD and the Anti-AUG nucleic acid constructs. Therefore, the previously described constructs may be used to block RNA packaging, as well as blocking RNA splicing and translation.

EXAMPLE 13

Blocking the poly-A Attachment Site

This embodiment is in accordance with the procedures and methods described in Example 1. Retroviral RNA is normally processed, like other mRNA's, by enzymatic splicing of a poly-A tail on the 3' end of the molecule. This is considered important for transport of the RNA out of the nucleus, and for stability in the cytoplasm. The previously described R region polynucleotide containing nucleic acid construct can produce complementary RNA capable of binding the poly-A attachment site and interfere with such RNA processing in this region.

EXAMPLE 14

Blocking of Dimer Formation and Genomic Folding

This embodiment is in accordance with the procedures and methods described in Example 1. Infectious retroviral particles contain two identical RNA genomic molecules which have regions of mutual hybridization i.e., dimer formation. They have as well, regions of internal hybridization and folding within each molecule. The exact role of these 3-dimensional configurations is unclear, but they appear to be universal and therefore important. The area of dimerization between the two molecules is in the U5, primer binding site, and leader regions. Therefore the previously described nucleic acid constructs can be used to block dimer formation and thereby interfere with internal hybridization and folding, within the individual molecules.

While the above-mentioned anti-viral molecules are simple complements of different regions of the retroviruses, more complex nucleic acid constructs can be employed to enhance antiviral activity. These are described below:

EXAMPLE 15

Compound Polynucleotides

This embodiment is in accordance with the procedures and methods described in Example 1. Compound polynucleotides can be synthesized which will code for mRNA consisting of tandem repeats of the same anti-viral sequence, or chimeric mRNA's containing more than one anti-viral sequence. These compound polynucleotides can then be inserted into a nucleic acid construct. By this method, the same promoter can transcribe proportionately more anti-viral material. Chimeric mRNA may have the added anti-viral trait of cross-linking different parts of the virus, disrupting genomic structure and function.

EXAMPLE 16

False Templates

The previous illustrative embodiments employ nucleic acid constructs, which when transcribed, produce RNA complementary to one or more essential hybridization sites within the retroviral genome. However, this particular embodiment illustrates use of a nucleic acid construct, which when transcribed, produces RNA corresponding to sites within the retroviral genome. This "corresponding" RNA can be used to inhibit one or more steps of the retroviral infection process by competing with the viral RNA for viral and/or cellular enzymes utilized by the virus in the infection process.

This embodiment is in accordance with the procedures and methods described in Example 1. The reverse transcriptase enzyme of the virus can be used against itself, through the use of false templates. As already mentioned, certain RNA sequences serve as initiation sites for reverse transcription (i.e., the primer binding site, herein after PBS), or serve as re-initiation sites for reverse transcription (i.e., the R region, and the PBS region, at the first and second jump events, respectively). Reverse transcription normally begins from these sequences, and any sequence 5' from these sequences will be automatically reverse transcribed. By introducing nucleic acid constructs, which when transcribed, produce RNA corresponding (sense) to the PBS and/or R regions, false templates are produced which can compete with viral RNA for viral and/or cellular enzymes. These false templates have the original anti-viral activities of the R and PBS molecules. In addition, they have several new properties: a) In the case of initiating reverse transcription, the PBS false template will bind and "disarm" reverse transcriptase complexes; b) In terms of re-initiating reverse transcription after the first and second jumps, false templates will lead the reverse transcription process down a "false path", leaving the original template destroyed, and the new cDNA abortive; c) Because the false templates will be reverse-transcribed, cDNA complementary to the 5' end of the molecule will be created by the reverse transcriptase enzyme. The resulting DNA sequence may have still further anti-viral activity. For example, if the 5' RNA sequence employed in the false template was a complement of the poly-purine tract, the resulting cDNA would be the DNA equivalent of the poly-purine tract, which would stably bind to the initiation site for second strand DNA synthesis, blocking correct initiation of DNA synthesis from this point.

In accordance with the procedures and methods described in Example 2, plasmids were constructed to express a corresponding ("sense") transcript to the FIV LTR and PBS regions. To evaluate whether resistance to FIV infection was conferred on cells containing a nucleic acid construct which expresses a transcript corresponding to the FIV LTR and PBS regions, cells of feline lymphocyte cell line 3201 were transfected with plasmid S6.8 Also, cells were transfected with AAV vector LNSX which served as a control (designated "WT"). The transfected feline cells were challenged with the feline petaluma isolate of FIV at a multiplicity of 5 to 10 $TCID_{50}$. Cells were maintained in medium without G418 during the FIV challenge, and the challenged cells were monitored for virus production by measuring reverse transcriptase released into the medium. Reverse transcriptase was measured using poly(ra): oligo(dt) as a template primer, as described previously by Heine et alo (1980 *J. Gen. Virol.* 49:385).

Some inhibition of reverse transcriptase activity was seen in FIV challenged feline cells transfected with nucleic acid construct S6.8 (FIG. 4, □), when compared to the reverse transcriptase activity detected in FIV challenged cells transfected with LNSX alone (●).

In accordance with the procedures and methods described in Example 3, plasmids were constructed to express a corresponding ("sense") transcript to the HIV LTR and PBS regions. To evaluate whether resistance to HIV infection was conferred on cells containing a nucleic acid construct which expresses a transcript corresponding to the HIV LTR and PBS regions, cells of human lymphocyte cell line CEM were electroporated with pHIV21. The transfected feline cells were challenged with dilutions of virus-containing culture supernatant (BP-1 isolate of HIV), and the challenged cells were monitored for virus production by assaying the culture supernatant from the challenged cells for HIV P24 core antigen using a commercial ELISA kit.

Upon stably transfecting the human lymphocyte cell line with a vector expressing transcripts corresponding to the 5'LTR and PBS regions in the HIV genome, sense-mediated inhibition of HIV infection was demonstrated. As illustrated in FIG. 5, P24 antigen detection was reduced in CEM cells containing pHIV21 ("sense") when compared to CEM cells without any nucleic acid construct ("CEM"). The reduction in P24 antigen detection was seen with HIV challenge at both a 1:25 dilution and a 1:50 dilution of virus-containing culture supernatant. Sense-mediated inhibition of viral infection, as measured by reduction in P24 antigen detection, continued to be observed for greater than 10 days post-transfection.

EXAMPLE 17

False Primers

This embodiment is in accordance with the procedures and methods described in Example 1. False primers can be created by placing a lysine tRNA sequence at the 5' end of any of several of the types of nucleic acid constructs already discussed. The result will be a modified lysine tRNA, which will have lost its original site for binding to the PBS. Instead, the modified lysine tRNA will bind at a different part of the viral genome, as dictated by the specific complementary "tail" selected. Consequently, the resulting false primer will complex with reverse transcriptase enzyme, and will initiate reverse transcription at an improper site. This will cause the viral template to be progressively degraded from that point, and will result in abortive and non-infectious cDNA with improper "ends" required for circularization and insertion.

We claim:

1. A method of conferring resistance to retroviral infection upon a host cell by inhibiting in the infection process at least one step of the process selected from the group consisting of retroviral replication, reverse transcription, and translation, said method comprising:

introduction into said host cell in vitro of a vector comprising a polynucleotide which is transcribed to RNA, within said host cell, said RNA is complementary to a nucleic acid sequence within at least one region within the genome of said retrovirus, wherein said region is an essential hybridization site within the retroviral genome selected from the group consisting of the LTR region, the U5 region, the U3 region, the 3'R region, the primer binding (PBS) region, the AUG start codon region, the polyp region, the cap site, the leader region, and RNA splice sites; and wherein said retrovirus is selected from the group consisting of the HIV, FIV, HTLV-I, HTLV-II, and FeLV.

2. The method of claim 1, wherein said polynucleotide is a synthetic polynucleotide.

3. The method of claim 1, wherein said polynucleotide is DNA.

4. The method of claim 1, wherein said vector is selected from the group consisting of a viral vector, a retroviral vector and a plasmid.

5. The method of claim 4, wherein said vector is a plasmid.

6. The method of claim 1, wherein said polynucleotide directs transcription of a single RNA which is complementary to multiple sites within the retrovirus genome.

7. The method of claim 4, wherein said vector further comprises a promoter which controls transcription of said RNA within said host cell.

8. The method of claim 4, wherein said vector further comprises a terminator which controls termination of transcription of said RNA within said host cell.

9. The method of claim 4, wherein said vector further comprises a marker for selection of transformed cells.

10. The method of claim 4, wherein said polynucleotide further comprises a promoter which controls transcription of said RNA within said host cell.

11. The method of claim 10, wherein said promoter is RNA Polymerase III promoter.

12. The method of claim 4, wherein said polynucleotide further comprises a terminator which controls termination of transcription of said RNA within said host cell.

13. The method of claim 12, wherein said terminator is a RNA Polymerase III terminator sequence.

14. A method of conferring resistance to retroviral infection upon a host cell by inhibiting in the infection process at least one step of the process selected from the group consisting of retroviral replication, reverse transcription, and translation, said method comprising:

Introduction into said host cell in vitro of a vector comprising a polynucleotide which is transcribed to RNA, within said host cell, said RNA corresponds to a nucleic acid sequence within at least one region within the genome of said retrovirus, wherein said region is a site that can bind a retroviral protein and is selected from the group consisting of the LTR region, the U5 region, the U3 region, the 3'R region, and the primer binding (PBS) region; and wherein said retrovirus is selected from the group consisting of HIV, FIV, HTLV-I, HTLV-II, and FeLV.

15. The method of claim 14, wherein said polynucleotide is a synthetic polynucleotide.

16. The method of claim 14, wherein said polynucleotide is DNA.

17. The method of claim 14, wherein said vector is selected from the group consisting of a viral vector, a retroviral vector, and a plasmid.

18. The method of claim 17, wherein said vector is a plasmid.

19. The method of claim 14, wherein said polynucleotide directs transcription of a single RNA which corresponds to multiple sites within the retrovirus genome.

20. The method of claim 17, wherein said vector contains a promoter which controls transcription of said RNA within said host cell.

21. The method of claim 17, wherein said polynucleotide contains a promoter which controls transcription of said RNA within said host cell, and a terminator which controls termination of said transcription.

22. The method of claim 21, wherein said promoter is RNA Polymerase III promoter sequence, and said terminator is RNA Polymerase III terminator sequence.

23. A nucleic acid construct conferring resistance to retroviral infection upon a host cell by inhibiting in the infection process at least one step of the process selected from the group consisting of retroviral replication, reverse transcription, and translation, said construct comprising a polynucleotide which when introduced by a vector into the host cell in vitro results in transcription of the polynucleotide into RNA wherein the RNA is selected from the group consisting of:

(a) RNA complementary to a nucleic acid sequence within at least one region within the genome of said retrovirus, wherein said region is an essential hybridization site within the retroviral genome selected from the group consisting of the LTR region, the U5 region, the U3 region, the 3'R region, the primer binding (PBS) region, the AUG start codon, the polyP region, the cap site, the leader region, and RNA splice sites; and (b) RNA corresponding to a nucleic acid sequence within at least one region within the genome of said retrovirus, wherein said region is a site that can bind a retroviral protein and is selected from the group consisting of the LTR region, the U5 region, the U3 region, the 3'R region, and the primer binding (PBS) region;

wherein said retrovirus is selected from the group consisting of HIV, FIV, HTLV-I, HTLV-II, and FeLV.

24. The nucleic acid construct of claim 23, wherein said polynucleotide is a synthetic polynucleotide.

25. The nucleic acid construct of claim 23, wherein said polynucleotide is DNA.

26. The nucleic acid construct of claim 23, wherein said vector is selected from the group consisting of a viral vector, a retroviral vector and a plasmid.

27. The nucleic acid construct of claim 26, wherein said vector is a plasmid.

28. The nucleic acid construct of claim 26, wherein said vector contains a promoter which controls transcription of said RNA within said host cell, and a terminator which controls termination of said transcription.

29. The nucleic acid construct of claim 26, wherein said vector contains a marker for selection of transformed cells.

30. The nucleic acid construct of claim 26, wherein said polynucleotide contains a promoter which controls transcription of said RNA within said host cell, and a terminator which controls termination of said transcription.

31. The nucleic acid construct of claim 30, wherein said promoter is RNA Polymerase III promoter, and said terminator is RNA Polymerase III terminator.

32. A cell modified by the method of claim 1.

33. A cell modified by the method of claim 14.

34. Progeny of the cell according to claim 32.

35. Progeny of the cell according to claim 33.

36. A RNA molecule, produced from the transcription of a polynucleotide of a nucleic acid construct which has been introduced into a host cell in vitro, wherein said RNA molecule confers resistance to retroviral infection upon a host cell by inhibiting in the infection process at least one step of the process selected from the group consisting of retroviral replication, reverse transcription, and translation, and said RNA is selected from the group consisting of:

(c) RNA complementary to a nucleic acid sequence within at least one region within the genome of said retrovirus, wherein said region is an essential hybridization site within the retroviral genome selected from the group consisting of the LTR region, the U5 region, the U3 region, the 3'R region, the primer binding (PBS) region, the AUG start codon, the polyP region, the cap site, the leader region, and RNA splice sites; and (d) RNA corresponding to a nucleic acid sequence within at least one region within the genome of said retrovirus, wherein said region is a site that can bind a retroviral protein and is selected from the group consisting of the LTR region, the U5 region, the U3 region, the 3'R region, and the primer binding (PBS) region;

wherein said retrovirus is selected from the group consisting of HIV, FIV, HTLV-I, HTLV-II, and FeLV.

37. The RNA molecule of claim 36, wherein the nucleic acid construct contains a promoter which controls transcription of said RNA within said host cell, and a terminator which controls termination of said transcription.

38. The RNA molecule of claim 36, wherein said nucleic acid construct further comprises a marker for selection of transfected cells.

39. The RNA molecule of claim 37, wherein said promoter is RNA Polymerase III promoter, and said terminator is RNA Polymerase III terminator sequence.

40. The RNA molecule of claim 36, wherein the RNA, corresponding to a nucleic acid sequence within the genome of said retrovirus, acts as a false template for retroviral reverse transcriptase enzyme resulting in competition for the enzyme between said false template and retroviral RNA template.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 355 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE:
        ( A ) LIBRARY: plasmid
        ( B ) CLONE: pBH10

( i v ) ORIGINAL SOURCE:
        ( A ) ORGANISM: Human Immunodeficiency Virus
        ( B ) STRAIN: BH10
        ( C ) CELL TYPE: virus ( v ) FEATURE:
        ( A ) OTHER INFORMATION: contains part of U3 region and
            contains the U5, R, and PBS regions ( v i ) SEQUENCE DESCRIPTION: SEQ ID NO: 1:

```
GAGCTTGCTA  CAAGGGACTT  TCCGCTGGGG  ACTTTCCAGG  GAGGCGTGGC      50
CTGGGCGGGA  CTGGGGAGTG  GCGAGCCCTC  AGATCCTGCA  TTTTAGCAGC     100
TGCTTTTTGC  CTGTACTGGG  TCTCTCTGGT  TAGACCAGAT  CTGAGCCTGG     150
GAGCTCTCTG  GCTAACTAGG  GAACCCACTG  CTTAAGCCTC  AATAAAGCTT     200
GCCTTGAGTG  CTTCAAGTAG  TGTGTGCCCG  TCTGTTGTGT  GACTCTGGTA     250
ACTAGAGATC  CCTCAGACCC  TTTTAGTCAG  TGTGGAAAAT  CTCTAGCAGT     300
GGCGCCCGAA  CAGGGACCTG  AAAGCGAAAG  GGAAACCAGA  GCTCTCTCGA     350
CGCAG                                                           355
```

( 2 ) INFORMATION FOR SEQ ID NO:2:

( i ) SEQUENCE CHARACTERISTICS:
        ( A ) LENGTH: 289 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: Feline Immunodeficiency Virus
        ( B ) STRAIN: Petaluma
        ( C ) CELL TYPE: virus ( v ) FEATURE:
        ( A ) OTHER INFORMATION: contains part of U3 region and
            contains the U5, R, and PBS regions ( v i ) SEQUENCE DESCRIPTION: SEQ ID NO: 2:

```
CTTGCTAATG  ACGTATAAGT  TGTTCCATTG  TAAGAGTATA  TAACCAGTGC      50
TTTGTGAAAC  TTCGAGGAGT  CTCTTTGTTG  AGGACTTTTG  AGTTCTCCCT     100
TGAGGCTCCC  ACAGATACAA  TAAATATTTG  AGATTGAACC  CTGTCGAGTA     150
TCTGTGTAAT  CTTTTTTACC  TGTGAGGTCT  CGGAATCCGG  GCCGAGAACT     200
```

```
TCGCAGTTGG  CGCCCGAACA  GGACTTGATT  GAGAGTGATT  GAGGAAGTGA           250

AGCTAGAGCA  ATAGAAAGCT  GTTAAGCAGA  ACTCCTGCT                        289
```

( 2 ) INFORMATION FOR SEQ ID NO:3:

( i ) SEQUENCE CHARACTERISTICS:
        ( A ) LENGTH: 720 nucleotides
        ( B ) TYPE: nucleic acid
        ( C ) STRANDEDNESS: single- stranded
        ( D ) TOPOLOGY: linear ( i i ) MOLECULE TYPE: RNA ( i i i ) IMMEDIATE SOURCE: genomic ( i v ) ORIGINAL SOURCE:
        ( A ) ORGANISM: HTLV-I
        ( B ) CELL TYPE: virus ( v ) FEATURE:
        ( A ) OTHER INFORMATION: contains LTR region ( v i ) SEQUENCE DESCRIPTION: SEQ ID NO: 3:

```
GGCUCGCAUC  UCUCCUCCAC  GCGCCCGCCA  CCCUACCUGA  GGCCUCCAUC            50

CACGCCGAUU  GAGUCGCGUU  CUGCCGCCUC  CCGCCUGUGG  UGCCUCCUGA           100

ACUGCGUCCG  CCGUCUAGGU  AAGUUUAAAG  CUCAGGUCGA  GACCGGGCCU           150

UUGUCCGGCG  CUCCCUUGGA  GCCUACCUAG  ACUCAGCCGG  CUCUCCACGC           200

UUUGCCUGAC  CCUGCUUGCU  CAACUCUACG  UCUUUGUUUC  GUUUUGUGUU           250

CUGCGCCGUU  ACAGAUCGAA  AGUUCCACCC  CUUUCCCUUU  CAUUCACGAC           300

UGACUGCCGG  CUUGGCCCAC  GGCCAAGUAC  CGGCGACUCC  GUUGGCUCGG           350

AGCCAGCGAC  AGCCCAUCCU  AUAGCACUCU  CAGGAGAGAA  AUUUAGUACA           400

CAGUUGGGGG  CUCGUCCGGG  AUACGAGCGC  CCCUUUAUUC  CCUAGGCAAU           450

GGGCCAAAUC  UUUUCCCGUA  GCGCUAGCCC  UAUUCCGCGA  CCGCCCCGGG           500

GGCUGGCCGC  UCAUCACUGG  CUUAACUUCC  UCCAGGCGGC  AUAUCGCCUA           550

GAACCCGGUC  CCUCCAGUUA  CGAUUCCAC  CAGUUAAAAA  AAUUUCUUAA            600

AAUAGCUUUA  GAAACACCGG  CUCGGAUCUG  UCCCAUUAAC  UACUCCCUCC           650

UAGCCAGCCU  ACUCCCAAAA  GGAUACCCCG  GCCGGGUGAA  UGAAAUUUUA           700

CACAUACUCA  UCCAAACCCA                                               720
```

( 2 ) INFORMATION FOR SEQ ID NO:4:

( i ) SEQUENCE CHARACTERISTICS:
        ( A ) LENGTH: 30 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: HTLV-I
        ( B ) CELL TYPE: virus ( v ) FEATURE:
        ( A ) OTHER INFORMATION: R region polynucleotide ( v i ) SEQUENCE DESCRIPTION: SEQ ID NO: 4:

```
GAAACAAAGA  CGTAGAGTTG  AGCAAACAGG                                    30
```

( 2 ) INFORMATION FOR SEQ ID NO:5:

( i ) SEQUENCE CHARACTERISTICS:
        ( A ) LENGTH: 20 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: HTLV-I
        ( B ) CELL TYPE: virus ( v ) FEATURE:
        ( A ) OTHER INFORMATION: CAP region polynucleotide ( v i ) SEQUENCE DESCRIPTION: SEQ ID NO: 5:

```
GTGAAGGAGA  GATGCGAGCC                                                          20
```

( 2 ) INFORMATION FOR SEQ ID NO:6:

( i ) SEQUENCE CHARACTERISTICS:
        ( A ) LENGTH: 70 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: FeLV
        ( B ) CELL TYPE: virus ( v ) FEATURE:
        ( A ) OTHER INFORMATION: R region polynucleotide ( v i ) SEQUENCE DESCRIPTION: SEQ ID NO: 6:

```
GATGCAAACA  GCAAGAGGCT  TTATTCGTAC  ACGGGTACCC  GGGCGGTCAA                      50

GTCTCAACAA  AGACTTGCGC                                                          70
```

( 2 ) INFORMATION FOR SEQ ID NO:7:

( i ) SEQUENCE CHARACTERISTICS:
        ( A ) LENGTH: 100 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: Human Immunodeficiency Virus
        ( B ) STRAIN: BH10
        ( C ) CELL TYPE: virus ( v ) FEATURE:
        ( A ) OTHER INFORMATION: R region polynucleotide ( v i ) SEQUENCE DESCRIPTION: SEQ ID NO: 7:

```
ACTTGAAGCA  CTCAAGGCAA  GCTTTATTGA  GGCTTAAGCA  GAGGGTTCCC                      50

TAGTTAGCCA  GAGAGCTCCC  AGGCTCAGAT  CTGGTCTAAG  CAGAGAGACC                     100
```

( 2 ) INFORMATION FOR SEQ ID NO:8:

( i ) SEQUENCE CHARACTERISTICS:
    ( A ) LENGTH: 70 nucleotides
    ( B ) TYPE: nucleic acid
    ( C ) STRANDEDNESS: double-stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: Feline Immunodeficiency Virus
    ( B ) STRAIN: Petaluma
    ( C ) CELL TYPE: virus ( v ) FEATURE:
    ( A ) OTHER INFORMATION: R region polynucleotide ( v i ) SEQUENCE DESCRIPTION: SEQ ID NO: 8:

```
GAGTCTCTTT GTTGAGGACT TTTGAGTTCT CCCTTGAGGC TCCCACAGAT         50

ACAATAAATA TTTGAGATTG                                          70
```

( 2 ) INFORMATION FOR SEQ ID NO:9:

( i ) SEQUENCE CHARACTERISTICS:
    ( A ) LENGTH: 30 nucleotides
    ( B ) TYPE: nucleic acid
    ( C ) STRANDEDNESS: double-stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: FeLV
    ( B ) CELL TYPE: virus ( v ) FEATURE:
    ( A ) OTHER INFORMATION: PBS region polynucleotide ( v i ) SEQUENCE DESCRIPTION: SEQ ID NO: 9:

```
GGGTCTCTAT CCCGGACGAG CCCCCAAATC                               30
```

( 2 ) INFORMATION FOR SEQ ID NO:10:

( i ) SEQUENCE CHARACTERISTICS:
    ( A ) LENGTH: 30 nucleotides
    ( B ) TYPE: nucleic acid
    ( C ) STRANDEDNESS: double-stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: HTLV-I
    ( B ) CELL TYPE: virus ( v ) FEATURE:
    ( A ) OTHER INFORMATION: PBS region polynucleotide ( v i ) SEQUENCE DESCRIPTION: SEQ ID NO: 10:

```
GCGCTCGTAT CCCGGACGAG CCCCCAACTG                               30
```

( 2 ) INFORMATION FOR SEQ ID NO:11:

( i ) SEQUENCE CHARACTERISTICS:
    ( A ) LENGTH: 25 nucleotides
    ( B ) TYPE: nucleic acid
    ( C ) STRANDEDNESS: double-stranded (D) TOPOLOGY: linear (ii) MOLECULE TYPE: DNA (iii) IMMEDIATE SOURCE: synthesized (iv) ORIGINAL SOURCE:
 (A) ORGANISM: HIV
 (B) STRAIN: BH10
 (C) CELL TYPE: virus (v) FEATURE:
 (A) OTHER INFORMATION: PBS region polynucleotide (vi) SEQUENCE DESCRIPTION: SEQ ID NO: 11:

GTCCCTGTTC GGGCGCCACT GCTAG                                                     25

(2) INFORMATION FOR SEQ ID NO:12:

(i) SEQUENCE CHARACTERISTICS:
 (A) LENGTH: 25 nucleotides
 (B) TYPE: nucleic acid
 (C) STRANDEDNESS: double-stranded
 (D) TOPOLOGY: linear (ii) MOLECULE TYPE: DNA (iii) IMMEDIATE SOURCE: synthesized (iv) ORIGINAL SOURCE:
 (A) ORGANISM: Feline Immunodeficiency Virus
 (B) STRAIN: Petaluma
 (C) CELL TYPE: virus (v) FEATURE:
 (A) OTHER INFORMATION: PBS region polynucleotide (vi) SEQUENCE DESCRIPTION: SEQ ID NO: 12:

GTTGGCGCCC GAACAGGACT TGATT                                                     25

(2) INFORMATION FOR SEQ ID NO:13:

(i) SEQUENCE CHARACTERISTICS:
 (A) LENGTH: 30 nucleotides
 (B) TYPE: nucleic acid
 (C) STRANDEDNESS: double-stranded
 (D) TOPOLOGY: linear (ii) MOLECULE TYPE: DNA (iii) IMMEDIATE SOURCE: synthesized (iv) ORIGINAL SOURCE:
 (A) ORGANISM: FeLV
 (B) CELL TYPE: virus (v) FEATURE:
 (A) OTHER INFORMATION: AUG region polynucleotide (vi) SEQUENCE DESCRIPTION: SEQ ID NO: 13:

CTAGAGGCTC CAGACATCAG ACACCCGTGG                                                30

(2) INFORMATION FOR SEQ ID NO:14:

(i) SEQUENCE CHARACTERISTICS:
 (A) LENGTH: 30 nucleotides
 (B) TYPE: nucleic acid
 (C) STRANDEDNESS: double-stranded
 (D) TOPOLOGY: linear (ii) MOLECULE TYPE: DNA (iii) IMMEDIATE SOURCE: synthesized ( i v ) ORIGINAL SOURCE:
    ( A ) ORGANISM: FeLV
    ( B ) CELL TYPE: virus ( v ) FEATURE:
    ( A ) OTHER INFORMATION: S region polynucleotide ( v i ) SEQUENCE DESCRIPTION: SEQ ID NO: 14:

TCGCCGGCCA GCTTACCTCC TGATGGTGGG 30

( 2 ) INFORMATION FOR SEQ ID NO:15:

( i ) SEQUENCE CHARACTERISTICS:
    ( A ) LENGTH: 30 nucleotides
    ( B ) TYPE: nucleic acid
    ( C ) STRANDEDNESS: double- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: HTLV-I
    ( B ) CELL TYPE: virus ( v ) FEATURE:
    ( A ) OTHER INFORMATION: S region polynucleotide ( v i ) SEQUENCE DESCRIPTION: SEQ ID NO: 15:

CTTTAAACTT ACCTAGACGG CGGACGCAGT 30

( 2 ) INFORMATION FOR SEQ ID NO:16:

( i ) SEQUENCE CHARACTERISTICS:
    ( A ) LENGTH: 30 nucleotides
    ( B ) TYPE: nucleic acid
    ( C ) STRANDEDNESS: double- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: HTLV-I
    ( B ) CELL TYPE: virus ( v ) FEATURE:
    ( A ) OTHER INFORMATION: AUG region polynucleotide ( v i ) SEQUENCE DESCRIPTION: SEQ ID NO: 16:

AGATTGGCCC ATTGCCTAGG GAATAAAGGG 30

( 2 ) INFORMATION FOR SEQ ID NO:17:

( i ) SEQUENCE CHARACTERISTICS:
    ( A ) LENGTH: 70 nucleotides
    ( B ) TYPE: nucleic acid
    ( C ) STRANDEDNESS: double- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: HIV
    ( B ) STRAIN: BH10
    ( C ) CELL TYPE: virus ( v ) FEATURE:
    ( A ) OTHER INFORMATION: combined S, GAG, and AUG regions
        polynucleotide ( v i ) SEQUENCE DESCRIPTION: SEQ ID NO: 17:

TGACGCTCTC GCACCCATCT CTCTCCTTCT AGCCTCCGCT AGTCAAAATT 50

TTTGGCGTAC TCACCAGTCG 70

( 2 ) INFORMATION FOR SEQ ID NO:18:

( i ) SEQUENCE CHARACTERISTICS:
        ( A ) LENGTH: 160 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: HIV
        ( B ) STRAIN: BH10
        ( C ) CELL TYPE: virus ( v ) FEATURE:
        ( A ) OTHER INFORMATION: combined PBS, AUG, GAG, and SD regions
            polynucleotide with RNA Polymerase III promoter and
            terminator ( v i ) SEQUENCE DESCRIPTION: SEQ ID NO: 18:

GATCCTAGTC AGACAGGCTT TTCAGGTCCC TGTTCGGGGG CCACTGCTAG 50

GAGATCAACT CCAGTTGACG CTCTCGCACC CATCTCTCTC CTTCTAGCCT 100

CCGCTAGTCA AAATTTTTGG CGTACTCACC AGTCGCCGCC CCTCGTTTTT 150

TTTTTAAGCT 160

( 2 ) INFORMATION FOR SEQ ID NO:19:

( i ) SEQUENCE CHARACTERISTICS:
        ( A ) LENGTH: 180 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: HIV
        ( B ) STRAIN: BH10
        ( C ) CELL TYPE: virus ( v ) FEATURE:
        ( A ) OTHER INFORMATION: combined R, and PBS regions
            polynucleotide with with RNA Polymerase III promoter and
            terminator ( v i ) SEQUENCE DESCRIPTION: SEQ ID NO: 19:

AGCTTTGGCA TAGTTGGCTT TTCAGGTCCC TGTTCGGGCG CCACTGCTAG 50

GAGTTCGAGA CCAGTACTTG AAGCACTCAA GGCAATCTTT ATTGAGGCTT 100

AAGCAGTGGG TCCCCTAGTT AGCCAGAGAG CTCCCAGGCT CAGATCTGGT 150

CTAACCAGAG AGACCTTTTT TTTTTGGATC 180

( 2 ) INFORMATION FOR SEQ ID NO:20:

( i ) SEQUENCE CHARACTERISTICS:
        ( A ) LENGTH: 150 nucleotides
        ( B ) TYPE: nucleic acid
        ( C ) STRANDEDNESS: double- stranded ( D ) TOPOLOGY: linear ( i i ) MOLECULE TYPE: DNA ( i i i ) IMMEDIATE SOURCE: synthesized ( i v ) ORIGINAL SOURCE:
      ( A ) ORGANISM: FeLV
      ( B ) CELL TYPE: virus ( v ) FEATURE:
      ( A ) OTHER INFORMATION: combined R, and PBS regions
      polynucleotide with with RNA Polymerase III promoter and
      terminator ( v i ) SEQUENCE DESCRIPTION: SEQ ID NO: 20:

| | | | | | |
|---|---|---|---|---|---|
| GATCCTTGGC | ATAGTTGGCT | GGGTCTCTAT | CCCGGACGAG | CCCCCAAATC | 50 |
| GGAGTTCGAG | ACCAGGATGC | AAACAGCAAG | AGGCTTTATT | CGTACACGGG | 100 |
| TACCCGGGCG | GTCAAGTCTC | AACAAAGACT | TGATCATTTT | TTTTTAAGCT | 150 |

( 2 ) INFORMATION FOR SEQ ID NO:21:

( i ) SEQUENCE CHARACTERISTICS:
      ( A ) LENGTH: 135 nucleotides
      ( B ) TYPE: nucleic acid
      ( C ) STRANDEDNESS: double- stranded
      ( D ) TOPOLOGY: linear ( i i ) MOLECULE TYPE: DNA ( i i i ) IMMEDIATE SOURCE: synthesized ( i v ) ORIGINAL SOURCE:
      ( A ) ORGANISM: FeLV
      ( B ) CELL TYPE: virus ( v ) FEATURE:
      ( A ) OTHER INFORMATION: combined PBS, AUG, and SD regions
      polynucleotide with with RNA Polymerase III promoter and
      terminator ( v i ) SEQUENCE DESCRIPTION: SEQ ID NO: 21:

| | | | | | |
|---|---|---|---|---|---|
| AGCTTGCAGT | CAGACAGGCA | CTATCCCGGA | CGAGCCCCCA | AATGAGAGTT | 50 |
| CAACTCCAGT | TCGCCGGCCA | GCTTACCTCC | TGATGGTGGG | CTAGAGGCTC | 100 |
| CAGACATCAG | ACACCCGCGG | TTTTTTTTT | GGATC | | 135 |

( 2 ) INFORMATION FOR SEQ ID NO:22:

( i ) SEQUENCE CHARACTERISTICS:
      ( A ) LENGTH: 140 nucleotides
      ( B ) TYPE: nucleic acid
      ( C ) STRANDEDNESS: double- stranded
      ( D ) TOPOLOGY: linear ( i i ) MOLECULE TYPE: DNA ( i i i ) IMMEDIATE SOURCE: synthesized ( i v ) ORIGINAL SOURCE:
      ( A ) ORGANISM: HTLV-I
      ( B ) CELL TYPE: virus ( v ) FEATURE:
      ( A ) OTHER INFORMATION: combined PBS, SD, and AUG regions
      polynucleotide with with RNA Polymerase III promoter and
      terminator ( v i ) SEQUENCE DESCRIPTION: SEQ ID NO: 22:

| | | | | | |
|---|---|---|---|---|---|
| GATCCGAGTC | AGACAGGCTT | TTCAGGTATC | CCCGGACGAG | CCCCCAACTG | 50 |
| GAGGTCGAGA | CCAGTCGTAG | AACTTACCTA | GACGGCGCAC | GCAGTAGATT | 100 |

GGCCCATTGC CCAGGGAATA AAGGGTTTTT TTTTTAAGCT                              140

( 2 ) INFORMATION FOR SEQ ID NO:23:

( i ) SEQUENCE CHARACTERISTICS:
        ( A ) LENGTH: 160 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: HTLV-I
        ( B ) CELL TYPE: virus ( v ) FEATURE:
        ( A ) OTHER INFORMATION: combined PBS, CAP, SD, R, and AUG
            regions polynucleotide with with RNA Polymerase III
            promoter and terminator ( v i ) SEQUENCE DESCRIPTION: SEQ ID NO: 23:

AGCTTTGGCA TAGTTGGCTT GCGTTCGTAT CCCGGACGAG CCCCCAACTG                    50

GAGTTCGAGA CCAGTGTGAA GGAGAGATGC GAGCCCTTTA AACTTACCTA                   100

GACGGCGGAC GCAGTGAAAC AAAGACGTAG AGTTAAGCAA GCAGGTTTTT                   150

TTTTTCGATC                                                              160

( 2 ) INFORMATION FOR SEQ ID NO:24:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) SEQUENCE DESCRIPTION: SEQ ID NO: 24:

ATCAAGCTTC TTGCTAATGA CGTATAAGT                                          29

( 2 ) INFORMATION FOR SEQ ID NO:25:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) SEQUENCE DESCRIPTION: SEQ ID NO: 25:

ATCAAGCTTA GCAGGAGTTC TGCTTAACA                                          29

( 2 ) INFORMATION FOR SEQ ID NO:26:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) SEQUENCE DESCRIPTION: SEQ ID NO: 26:

ATCAAGCTTA TCGAGCTTGC TACAAGGGA  29

( 2 ) INFORMATION FOR SEQ ID NO:27:

( i ) SEQUENCE CHARACTERISTICS:
        ( A ) LENGTH: 28 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) SEQUENCE DESCRIPTION: SEQ ID NO: 27:

ATCAAGCTTC TGCGTCGAGA GAGCTCTG  28